(12) United States Patent
Grodzins et al.

(10) Patent No.: US 9,014,339 B2
(45) Date of Patent: *Apr. 21, 2015

(54) VERSATILE X-RAY BEAM SCANNER

(75) Inventors: Lee Grodzins, Lexington, MA (US);
Jeffrey R. Schubert, Somerville, MA (US); Omar Al-Kofahi, Chelmsford, MA (US); Peter J. Rothschild, Newton, MA (US)

(73) Assignee: American Science and Engineering, Inc., Billerica, MA (US)

( * ) Notice: Subject to any disclaimer, the term of this patent is extended or adjusted under 35 U.S.C. 154(b) by 734 days.

This patent is subject to a terminal disclaimer.

(21) Appl. No.: 13/280,941

(22) Filed: Oct. 25, 2011

(65) Prior Publication Data

US 2012/0106714 A1 May 3, 2012

Related U.S. Application Data

(60) Provisional application No. 61/407,113, filed on Oct. 27, 2010, provisional application No. 61/533,407, filed on Sep. 12, 2011.

(51) Int. Cl.
*G21K 1/04* (2006.01)
*G21K 1/02* (2006.01)
*G02B 26/00* (2006.01)
*G02B 26/08* (2006.01)
(Continued)

(52) U.S. Cl.
CPC .............. *G01N 23/046* (2013.01); *G21K 1/02* (2013.01); *G21K 1/043* (2013.01); *G01N 2223/419* (2013.01)

(58) Field of Classification Search
USPC .......... 378/10–15, 57, 62, 91, 98.6, 119, 121, 378/140, 145–151, 156–160, 193, 204, 378/210; 250/505.1, 506.1, 507.1, 522.1; 359/641, 232–236
See application file for complete search history.

(56) References Cited

U.S. PATENT DOCUMENTS

| 1,648,687 A | 11/1927 | Hoxie | 348/201 |
| 2,825,817 A | 3/1958 | North | 378/146 |

(Continued)

FOREIGN PATENT DOCUMENTS

| DE | 1090784 | 10/1960 | |
| WO | 2007/111672 A3 | 10/2007 | G02B 26/10 |

OTHER PUBLICATIONS

Scitec Instruments "Optical Chopper Specials", www.scitec.uk.com 6 pages.

(Continued)

*Primary Examiner* — Anastasia Midkiff
(74) *Attorney, Agent, or Firm* — Sunstein Kann Murphy & Timbers LLP

(57) ABSTRACT

Apparatus for interrupting and/or scanning a beam of penetrating radiation, such as for purposes of inspecting contents of a container. A source, such as an x-ray tube, generates a fan beam of radiation effectively emanating from a source axis, with the width of the fan beam collimated by a width collimator, such as a clamshell collimator. An angular collimator, stationary during the course of scanning, limits the extent of the scan, and a multi-aperture unit, such as a hoop, or a nested pair of hoops, is rotated about a central axis, and structured in such a manner that beam flux incident on a target is conserved for different fields of view of the beam on the target. The central axis of hoop rotation need not coincide with the source axis.

22 Claims, 17 Drawing Sheets

(51) Int. Cl.
*G02B 26/10* (2006.01)
*G02B 27/09* (2006.01)
*G02B 27/30* (2006.01)
*G01N 23/04* (2006.01)

(56) References Cited

U.S. PATENT DOCUMENTS

| | | | | |
|---|---|---|---|---|
| 4,190,773 | A | * | 2/1980 | Braden et al. ............... 378/10 |
| 4,234,794 | A | | 11/1980 | Voinea et al. ............... 378/12 |
| 4,266,135 | A | * | 5/1981 | Kuwik et al. ............... 378/16 |
| 4,304,999 | A | * | 12/1981 | Richey et al. ............... 378/4 |
| 4,432,914 | A | | 2/1984 | Schifftner ............... 378/99 |
| 7,593,510 | B2 | | 9/2009 | Rothschild ............... 378/160 |
| 2003/0142783 | A1 | | 7/2003 | Daaland et al. ............... 378/55 |
| 2004/0120457 | A1 | | 6/2004 | Karellas et al. ............... 378/62 |
| 2006/0126792 | A1 | * | 6/2006 | Li ............... 378/147 |
| 2006/0233298 | A1 | | 10/2006 | Igarashi et al. ............... 378/19 |
| 2006/0245547 | A1 | | 11/2006 | Callerame et al. ............... 378/160 |
| 2007/0172031 | A1 | | 7/2007 | Cason et al. ............... 378/146 |
| 2009/0001296 | A1 | * | 1/2009 | Kuduvalli ............... 250/505.1 |
| 2009/0213984 | A1 | | 8/2009 | Warner et al. ............... 378/16 |
| 2012/0257710 | A1 | * | 10/2012 | Funk ............... 378/9 |

OTHER PUBLICATIONS

Korean Intellectual Property Office, Officer Kim International Search Report and Written Opinion, PCT/US2011/057648, date of mailing May 10, 2012, 9 pages.

* cited by examiner

VERSATILE X-RAY BEAM SCANNER

The present application claims the priority of U.S. Provisional Application Ser. No. 61/407,113, filed Oct. 27, 2010, and of U.S. Provisional Application Ser. No. 61/533,407, filed Sep. 12, 2011, both of which are incorporated herein by reference.

TECHNICAL FIELD

The present invention relates to methods and apparatus for interrupting, steering and/or varying the spatial sweep and resolution of a beam of radiation, and, more particularly, a beam used for x-ray inspection.

BACKGROUND ART

One application of x-ray backscatter technology is that of x-ray inspection, as employed, for example, in a portal through which a vehicle passes, or in a system mounted inside a vehicle for inspecting targets outside the vehicle. In such a system, an x-ray beam scans the target and detectors measure the intensity of backscattered radiation as the inspection vehicle and target pass each other. During inspection that images backscattered x-rays, it would be desirable for the operator to be able to control the x-ray beam's viewing angle, viewing direction, beam resolution and filtration.

SUMMARY OF EMBODIMENTS OF THE INVENTION

In accordance with embodiments of the invention, methods and apparatus are provided for scanning a beam of radiation with respect to a target. In certain embodiments, a scanning apparatus is provided for scanning a beam in a single dimensional scan. The apparatus has a source of radiation for generating a fan beam of radiation effectively emanating from a source axis and characterized by a width. The source also has an angle selector, stationary during the course of scanning, for limiting the extent of the scan, and a multi-aperture unit rotatable about a central axis in such a manner that beam flux incident on a target is conserved for different fields of view of the beam on the target. In some embodiments, there may also be width collimator for collimating the width of the fan beam.

In accordance with other embodiments of the invention, the angle selector may include a slot of continuously variable opening. The central axis may be substantially coincident with the source axis, or either forward-offset of rearward-offset relative to the central axis. The width collimator may include a variable slot collimator, fixed during the course of scanning the beam, adapted to change the sweep angle of the beam, up to a specified maximum angle, and to change a central direction of the sweep.

In accordance with yet other embodiments of the present invention, the source of radiation may be an x-ray tube, and may be a source of radiation of a type generating a fan beam exceeding 60° in opening angle. The scanning apparatus may also be coupled to a platform, and may have an enclosing conveyance for conveying the scanning apparatus past an inspection target. The scanning apparatus may be coupled to a platform in conjunction with at least one further scanning apparatus.

In accordance with alternate embodiments of the invention, the scanning apparatus may have a filter disposed within the beam for changing the energy distribution of the beam. The width collimator may have a variable-slot collimator fixed during x-ray scanning, to change the sweep angle of the x-ray beam, up to the maximum angle, as well as the direction of the sweep.

The multi-aperture unit may include two nested, multi-aperture collimators, and may include an inner multi-aperture hoop made of material opaque to the beam. The multi-aperture hoop may additionally include rings of apertures spaced laterally along the tube axis in such a manner that axial motion of the multi-aperture hoop places a ring of apertures in the beam that is collimated by a corresponding opening angle in the slot collimator. The multi-aperture unit may also include an outer multi-aperture hoop rotatable in registration with the inner multi-aperture hoop. The outer multi-aperture hoop may include a plurality of apertures configured as horizontal slots in such a manner as to define a minimum vertical size of emitted pencil beams. Where there are two multi-aperture hoops, the inner and outer multi-aperture hoops may be mechanically integral. There may be a variable width collimator for defining a width of the beam that enters the outer multi-aperture hoop. A variable width collimator may define a width of the beam that enters the outer multi-aperture hoop.

In other embodiments of the scanning apparatus, radiation may be emitted through a plurality of apertures at different angles with respect to the target, such that pencil beams of penetrating radiation sweep in alternation through the target in such a manner as to provide a stereoscopic view of an interior volume of the target. The scanning apparatus may have a rotation assembly adapted to provide for rotation of the source of radiation about the source axis. The multi-aperture unit may include substantially rectangular through-holes.

In accordance with alternate embodiments of the invention, a chopper is provided for interrupting a beam of particles, wherein the chopper has an obscuring element substantially opaque to passage of the particles in the propagation direction, and at least one through-hole in the obscuring element adapted for passage through the obscuring element of particles in the propagation direction, where the through-hole is characterized by a tapered dimension in a plane transverse to the propagation direction. Finally, the chopper has an actuator for moving the obscuring element in such a manner as to cause at least a portion of the beam of particles to traverse the at least one through hole on a periodic basis.

The through-hole of the chopper may be substantially conical or substantially biconical. The particles in the chopped beam may be massless, including electromagnetic radiation over a specified range of wavelengths.

In other alternate embodiments, a chopper is provided for interrupting a beam of particles that has an obscuring element substantially opaque to passage of the particles in the propagation direction and at least one through-hole in the obscuring element adapted for passage through the obscuring element of particles in the propagation direction, the through-hole characterized by a rectangular cross section in a plane transverse to the propagation direction.

In yet other alternate embodiments, a collimator is provided for narrowing a beam of a beam of particles, where the collimator has an obscuring element substantially opaque to passage of the particles in the propagation direction, and a gap in the obscuring element where the width of the gap varies as a function of distance along the long dimension relative to an edge of the gap. The gap may be fixed or adapted to be varied in at least one of the long and narrow dimensions.

In accordance with another embodiment of the invention, a beam chopping assembly is provided that has a rotating element including at least one through-hole of rectangular cross-section.

In yet other embodiments of the present invention, a method is provided for inspecting an object based on the transmission of x-rays through an object. The method has steps of:
 a. generating a fan beam of radiation;
 b. collimating the width of the fan beam with a collimator that is stationary during the course of a scan of the object, the scan characterized by an extent;
 c. limiting the extent of the scan with an angle selector; and
 d. varying a field of view of the beam on the object by means of a multi-aperture unit rotatable about a central axis in such a manner that beam flux incident on a target is conserved.

The method may also include varying a direction of the scan, and the step of varying a field of view may include varying from a primary rapid scan to a secondary high-resolution scan of a suspect area.

BRIEF DESCRIPTION OF THE DRAWINGS

The foregoing features of the invention will be more readily understood by reference to the following detailed description, taken with reference to the accompanying drawings, in which:

FIG. 3A shows a version of the angle selector that controls the angle of the fan beam from the x-ray tube, in accordance with an embodiment of the present invention, while

FIGS. 17A and 17B are perspective and cross-sectional views, respectively, of a biconical aperture (or through-hole) for beam chopping, in accordance with an embodiment of the present invention, while

DETAILED DESCRIPTION OF EMBODIMENTS OF THE INVENTION

Definitions.

As used herein, and in any appended claims, the following terms shall have the meanings indicated unless the context requires otherwise.

"Beam resolution," as used herein, shall refer to the product of a vertical resolution and a horizontal resolution. "Vertical" refers to the plane containing the swept pencil beam described herein, i.e., a plane perpendicular to the axis of rotation of the hoop described herein. The terms "horizontal" and "width" refer herein to the "axial" direction, which is to say, a direction parallel to the axis of rotation of the hoop(s) described herein.

"Resolution," in either of the foregoing vertical or horizontal cases, refers to the height (for instance, in angular measure, such as degrees, or minutes of arc, etc.) of the pencil beam when stationary on a stationary target, and the term assumes a point-like origin of the x-ray beam. Similarly, the areal beam resolution has units of square degrees or steradians, etc. Alternatively, resolution may be quoted in terms of a point spread function (PSF) at a specified distance from a defining aperture.

Figure 1:
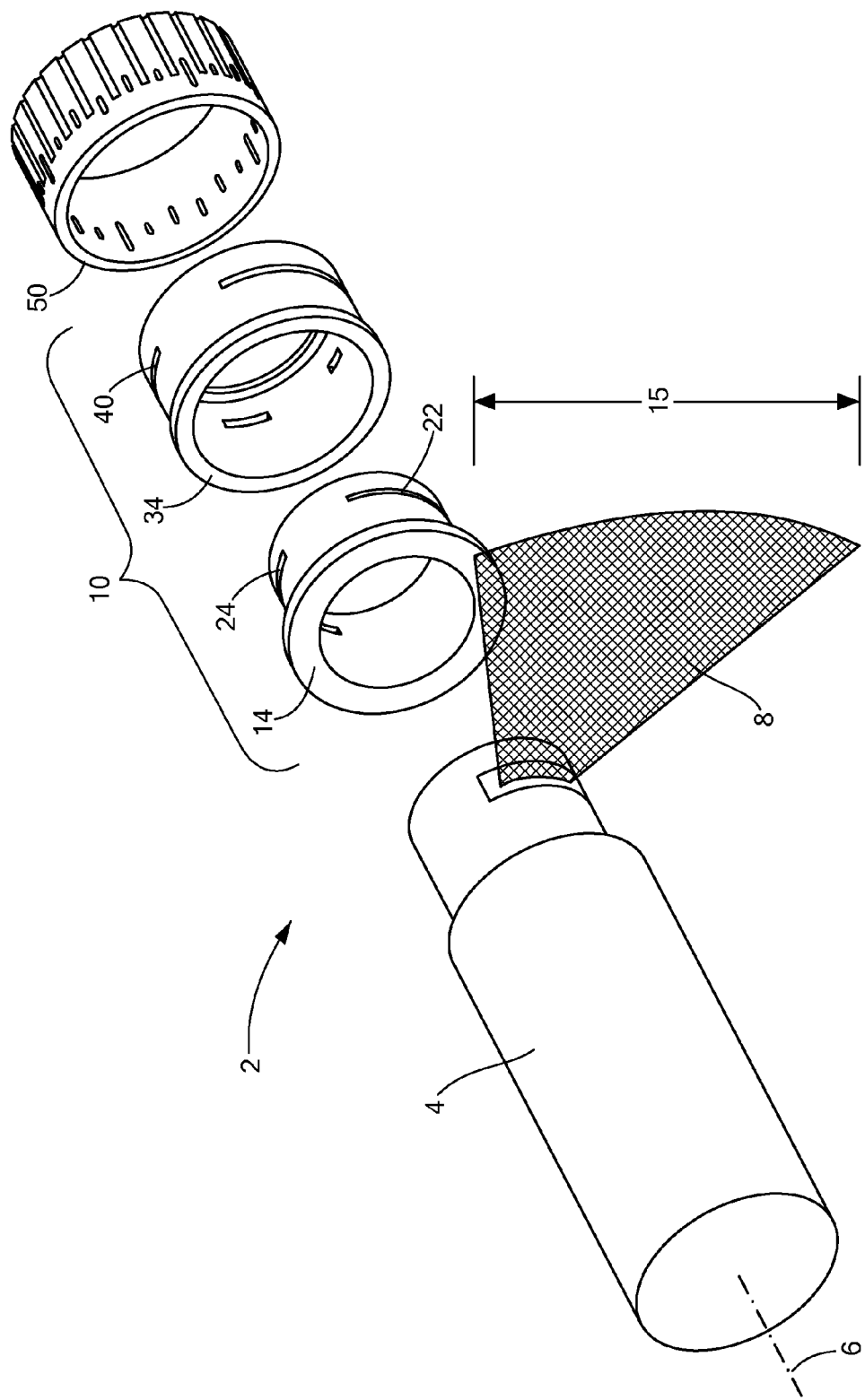
FIG. 1 shows an exploded view of major components of a basic unit in accordance with one embodiment of a versatile x-ray beam scanner.
Figure 2:
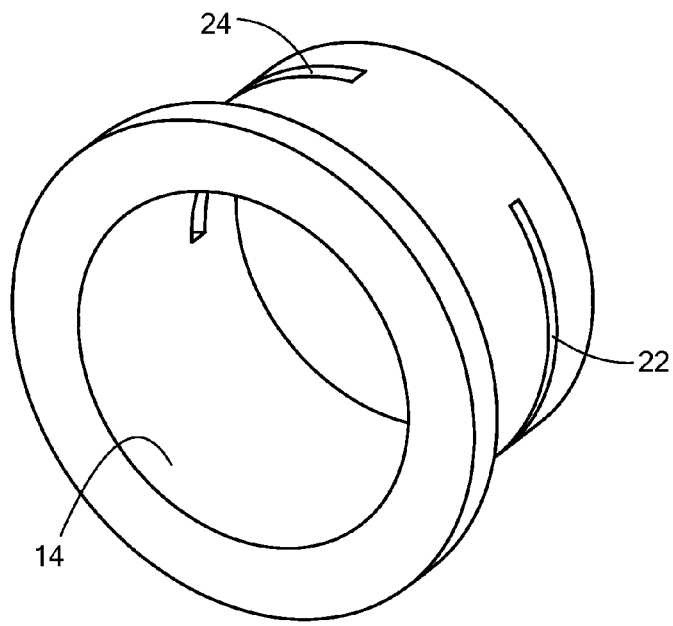
FIG. 2 depicts a version of a slot collimator used to control the width of a fan beam from an x-ray tube, in accordance with an embodiment of the present invention.

The "zoom angle" is the angular extent of the scanning x-ray beam in the vertical direction, designated by numeral 15 in FIG. 1.

The term "commensurate," as applied to angular intervals, refers to intervals related by whole number ratios, such that rotational cycles of distinct components repeat after a complete revolution of one component.

Preferred embodiments of the present invention provide a versatile beam scanner (VBS) (or, "flexible beam former" (FBF)), which may, particularly, refer to a mechanism in which the intensity of x-rays on a target increases inversely with the angular field of view on the target. While embodiments of the invention are described, herein, with reference to x-rays derived from an x-ray source, it is to be understood that various embodiments of the invention may advantageously be employed in the context of other radiation, whether electromagnetic or relating to beams of particles, and that all such embodiments are within the scope of the present invention.

It should also be understood that embodiments of the present invention may be applied to the formation of images of x-rays transmitted through a target as well as to the formation of images of x-rays scattered from the target, or for any application where steering and focusing a beam subject to conservation of beam flux might be advantageous.

In particular, in various embodiments of the present invention, a versatile beam scanner may advantageously be mounted on a vehicle or conveyance of any sort, or on a portal inspecting moving objects. Moreover, multiple versatile beam scanners may be mounted on a single portal or other platform, with beams temporally or spatially interleaved to preclude or reduce crosstalk.

The resolution of a beam on a target, where the beam is formed through a collimating hoop, is determined by the target's distance, and the height of the collimation slots in the outermost hoop. Methods, in accordance with embodiments of the present invention, provide for varying the height of the collimation slots for two distinct purposes: improving an image by improving the vertical resolution of the scanning pencil beam, and providing independent views with different vertical resolutions. These are discussed in detail, below.

Figure 7:
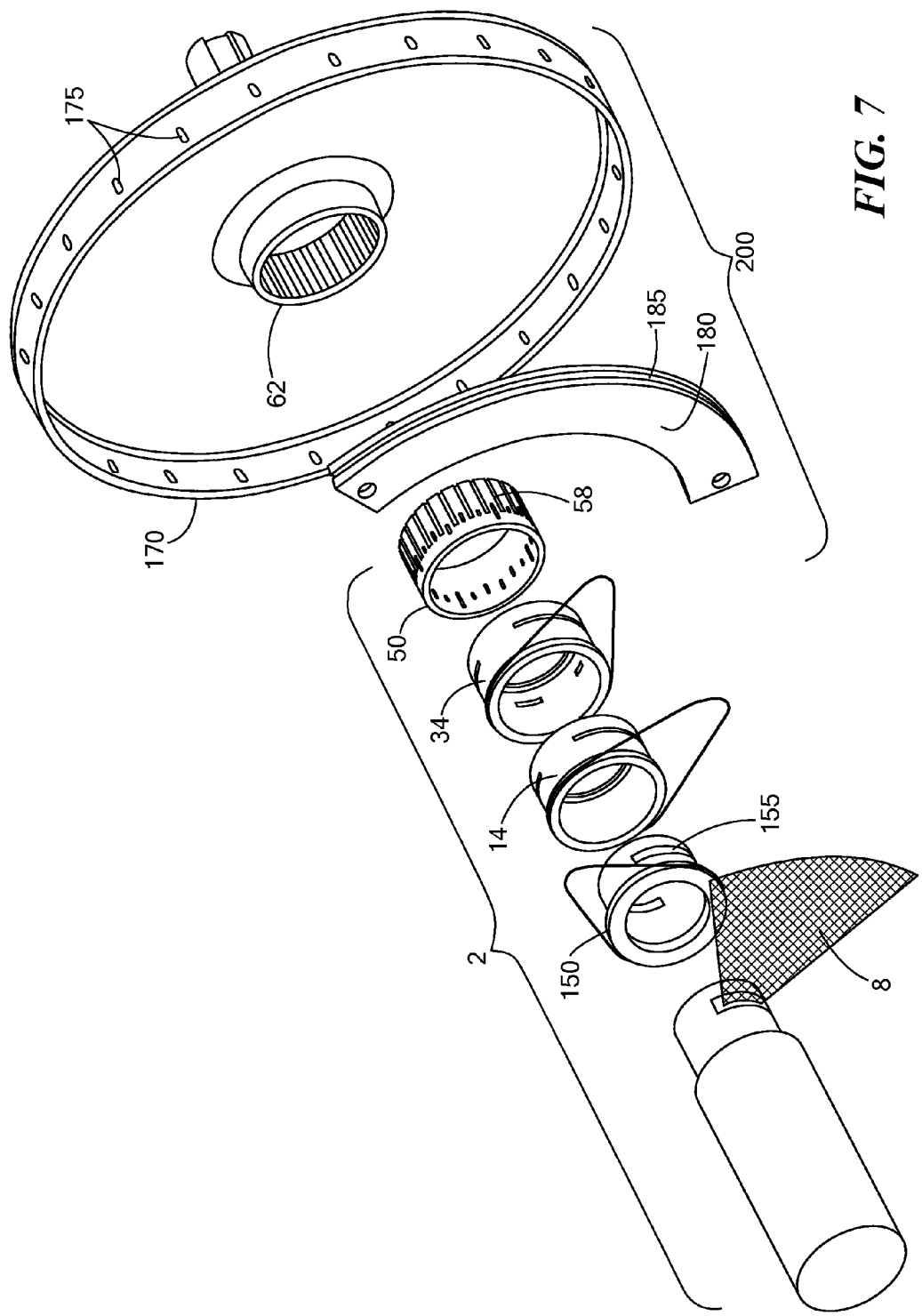
FIG. 7 is an exploded view of the full version of a versatile beam scanner showing the addition of a filter wheel, and the outer hoop with slot collimators and an inner width collimator with variable jaw spacing, in accordance with an embodiment of the present invention.

In accordance with preferred embodiments of the present invention, the axial (width) resolution is controlled with a variable collimator 180 (shown in FIG. 7). The angular (height resolution) is controlled by the integration time, and by two other parameters: the combination of wheel speed and scan angle, and a time constant associated with x-ray detection, namely the decay time of a scintillation phosphor. Typically, the integration time is set between 5 µs and 12 µs, with the number of resolved pixels in a vertical scan determined by the scan angle and rotational speed. For purposes of example, a hoop rotation rate of 3600 rpm, with 6 scans/revolution (as explained in detail below), and 500 pixels per scan, corresponds to ~6 µs integration, and a beam resolution of approximately 0.1° per pixel.

Basic elements of a VBS may be separated into a first part—an inner scanner, described with reference to FIG. 1, and designated generally by numeral 2, that is common to many embodiments, and a second part—an outer scanner 200 (shown in FIG. 7), that may be omitted for some applications. While, for purposes of explanation herein, the elements are summarized as a series of elements with increasing radii, it is to be understood that the order of the elements in the inner scanner can be varied. Elements of the VBS may include:

a source 4 of penetrating radiation, such as an x-ray tube, that emits a fan beam 8 of x-rays over a wide angle, preferably greater than 60°, such as 120°, and in a plane (referred to, herein, as the "vertical" plane) that is typically perpendicular to the direction of vehicle and target passage;

a selectable filter 150 (shown in FIG. 7) to change the energy distribution of the x-ray beam;

a slot collimator 14 and angle selector 34 in the plane of the x-ray beam, made of material that is opaque to the x-ray beam, that control the scan angle and scan direction;

a multi-aperture tube 50, made of material opaque to the x-rays, which rotates through the fan beam created by the slot-collimator to create a sweeping pencil beam;

a slotted collimator 180 (shown in FIG. 7), stationary during scanning, having an adjustable jaw width 185 that controls the horizontal width of the x-ray beam that inspects the target; and an outer aperture-collimator hoop 170 (shown in FIG. 7) that rotates in registration with the inner tube.

Referring to FIG. 1, the selectable widths of slot 22 (and 24) of slot collimator 14 defines the width of fan beam 8, which is emitted from x-ray tube 4 and effectively emanates at, or near, a source axis 6. The maximum opening angle is the x-ray tube's beam angle; it defines the maximum angular sweep 15 of the pencil beam. The opening angle for inspecting a target (not shown) can be changed, either by the operator or by automation, in fixed steps commensurate with 360°, with the maximum angle, as stated, limited by the x-ray tube's beam angle. The variable-slot collimator 34 can be rotated to change the direction of the sweep. Slot collimator 34 typically remains fixed during the course of scanning.

Figure 3A:
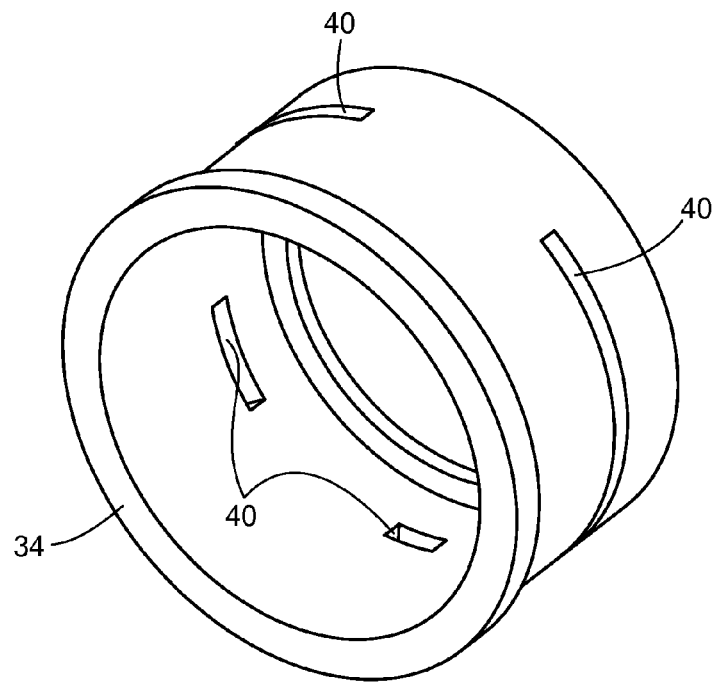
Figure 3B:
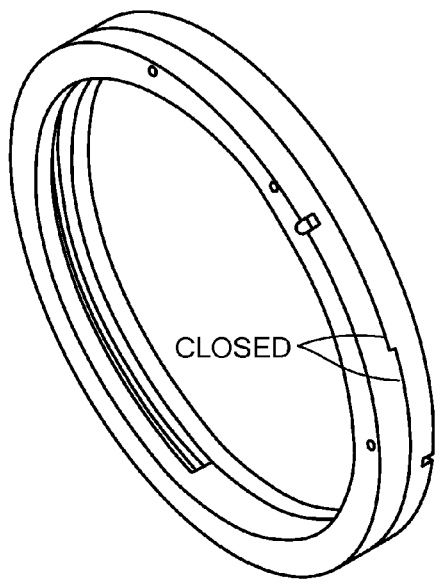
FIGS. 3B-3E show views of a continuously variable angle selector in accordance with a further embodiment of the present invention.
Figure 3C:
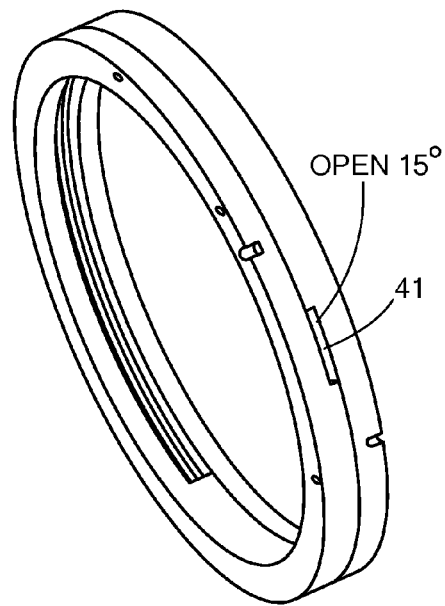
Figure 3D:
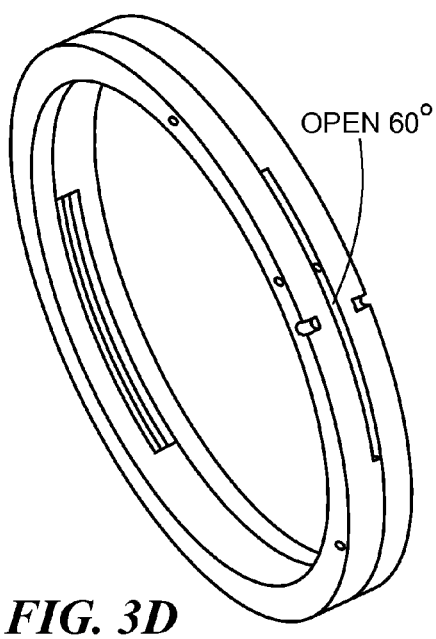
Figure 3E:
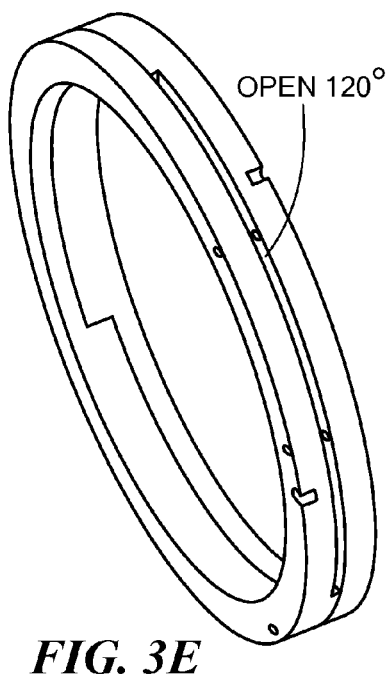
Figure 4:
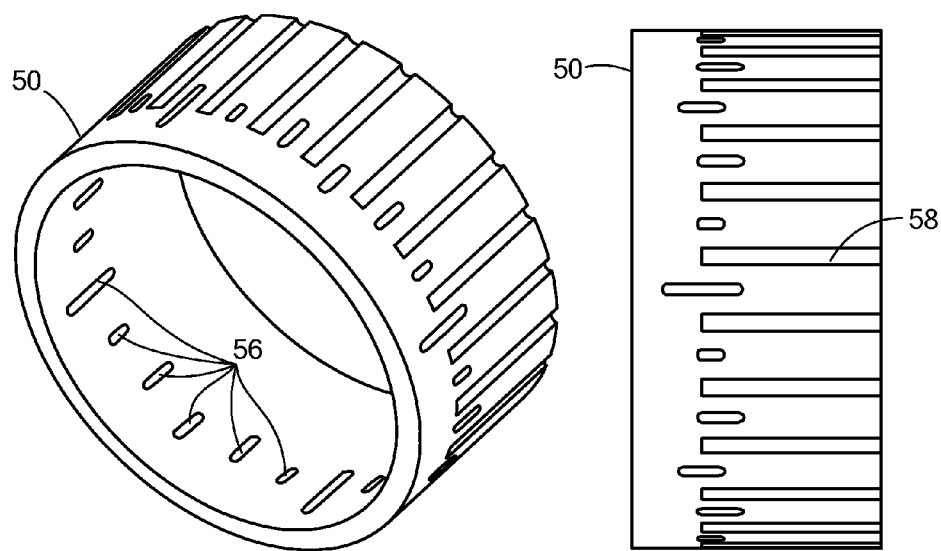
FIG. 4 shows a multi-slot aperture tube that rotates to create the scanning pencil beam, in accordance with an embodiment of the present invention.
Figure 5:
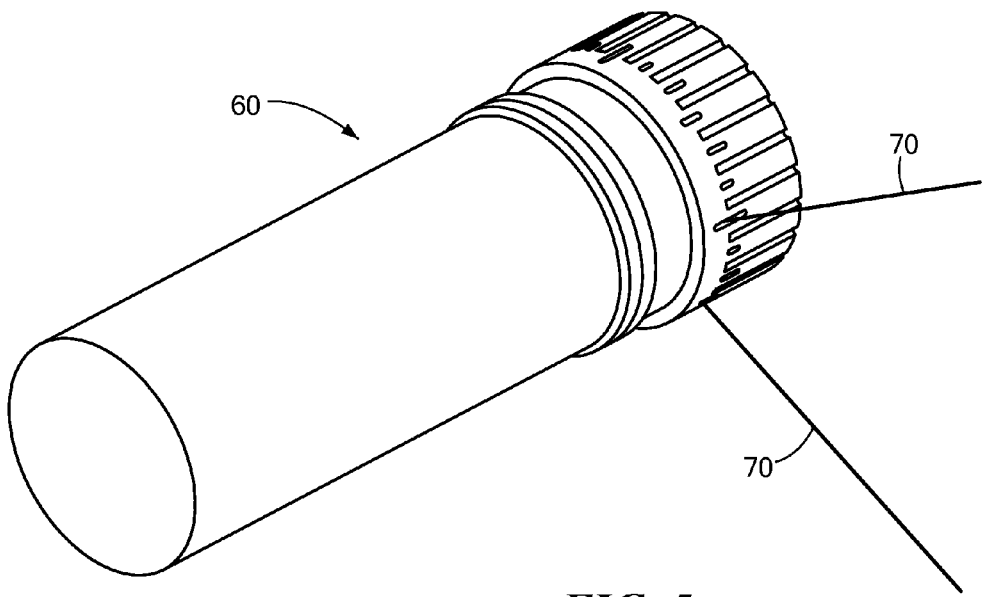
FIG. 5 shows an assembly view of a basic versatile beam scanner, in accordance with an embodiment of the present invention.

Angle selector 34 has rings of apertures 40 (best seen in FIG. 3A) that define the height of the pencil beam 70. The combination of the slot collimator 14 and the aperture 40 in angle selector 34 defines the cross-section of pencil beam 70 (shown in FIG. 4). Each lateral ring of apertures 40 corresponds to one of the quantized opening angles of variable-slot collimator 14. When one of the opening angles of slot collimator 14 is chosen, angle selector 34 is moved laterally to place the appropriate ring of apertures in the beam. The number of apertures in each ring is commensurate with 360°. Alternatively, angle selector 34 may provide for continuous variation of opening angle from closure (as shown in FIG. 3B) to an opening of 120° (as shown in FIG. 3E), with other opening angles shown by way of example.

The zoom angle, i.e., the angular extent of the scanning x-ray beam, may be determined by the lateral position of the spinning hoop(s) 50 and 170. "Lateral," as used herein, refers to a position along an axis parallel to the axis 6 about which hoops 50 and 170 rotate. In order to change that lateral position (and, thereby, the zoom angle), the plane of the fan beam is varied (in a step-wise fashion) with respect to the plane of apertures that define the zoom angle. In a preferred embodiment of the invention, the aperture hoop(s), which are rotating at high speed, are not be translated, but, rather, the rest of the beam forming system is translated with respect to rotating aperture hoop(s), however, it is to be understood that either configuration falls within the scope of the present invention.

When the target (not shown) is distant from the inner scanner 2, the outer unit 200 is used to further define the cross-section of the pencil beam at the target. Referring now to FIG. 7, the outer unit 200 consists of a slot-collimator 180 (shown in FIG. 7) to refine the width of the scanning beam, and a rotating hoop 170 with apertures 175 to refine the height of the pencil beam 70. The apertures 175 in the outer hoop 170 are equally-spaced, and their number is equal to the maximum number of apertures in a ring of the inner multi-aperture tube 50. The number is also commensurate with the number of apertures in each of the rings of the inner beam-forming unit. The outer hoop is light-weight, thereby advantageously reducing its rotational moment of inertia. The beam defining apertures are typically tungsten inserts.

A slotted collimator 180 (shown in FIG. 7), with adjustable jaw width, controls the horizontal width of the x-ray beam that inspects the target, and is stationary during scanning.

One novel and advantageous feature of embodiments of the present invention is the focusing feature. The decrease of the scan angle—in order to focus on a portion of the target—results in a corresponding increase in the beam intensity, since the number of slots per revolution of the hoop increases as the scan angle decreases. Thus, for example, the total flux of x-rays in a 15° view is six times greater than in a 90° view of the target. A further novel feature is the operator's ability to change the cross-section of the scanning pencil beam by moving the jaws of the fixed collimator 14, or the variable collimator 180, to change the width of the image pixel, and changing the integration time of the detected signal to change the height of the image pixel. Yet another novel feature is the operator control of the viewing direction of the x-ray scan.

The flexible beam former, in accordance with the various embodiments taught herein, may be advantageously applied to the formation of images of x-rays transmitted through a target or to the formation of images of x-rays scattered from the target. It can be applied to a scan taken by rotating the scanning system. It can be implemented by manual changes carried out when the scanner is turned off, though the preferred embodiment is for changes carried out during the scan and even automatically in response to programmed instructions.

The versatility of the x-ray scanners taught herein allows the operator to obtain the most effective inspection for targets at distances and relative traversal speeds that can each vary over more than an order of magnitude.

Without loss of generality, the apparatus and methods described herein may be applied here to image formation of x-rays backscattered from a target that moves perpendicularly at constant speed through the plane of the scanning pencil beam.

Embodiments of the invention, in several variants, are now described with reference to FIGS. 1 to 8. In a preferred embodiment, described with particular reference to FIGS. 1-7, a single beam of x-rays is produced, under operator or automatic control, that scans the target through selected angles of 90°, 45°, 30°, or 15°, with a chosen cross-section, at the target. The 90° opening is the normal position; the three other openings provide 2×, 3× and 6× zooming. Of course, it will be understood that the basic concepts described herein may readily be applied to applications that may involve a different number of different scanning angles as well as different x-ray energies. The concepts can also be applied to the creation of beams that scan at different inclination angles through the target.

Referring to FIG. 1, a scanning apparatus is designated generally by numeral 2. An x-ray tube 4 produces a 90° fan beam of x-rays 8 that is emitted perpendicular to the x-ray tube axis 6. An angle-defining unit 10, which is stationary during a beam scan, intercepts the beam 8. The angle-defining unit 10 defines the width and angle of the fan beam, either through operator control or automatically according to external criteria. In a preferred embodiment, the angle-defining unit 10 is a variable slot shown in a simplified version in FIGS. 3B-3E. Angle-defining unit 10 is opaque to the x-ray beam 8 except for the continuously-variable slot 41 (shown in FIG. 3C, by way of example), whose opening angle and pointing direction may be controlled by servo motors. FIG. 3B shows the slot closed, while FIGS. 3C-3E show opening angles of 15°, 60° and 120°, respectively.

It should be noted that alternate methods for obtaining the versatility provided by tubes 14 and 34 are within the scope of the present invention. Further versatility can be provided by rotating the entire x-ray producing unit including the x-ray tube itself, as further described below.

Angle-defining tubes 14 and 34 can be rotated so that opaque sections of both tubes intercept the exiting beam without shutting down the x-ray tube or the beam-forming wheels. Rotation of the unit 10 allows the sweeping beam to point in any directions inside the maximum fan beam 8 from the x-ray tube. Further versatility in aiming the fan beam can be obtained by rotations of the entire x-ray generator. Angle selector 34, or another element, may serve as an x-ray shutter, whose power-off position is closed, to shutter the x-ray beam to comply with safety regulations. The shutter can be combined with other features such as the filter changer.

Sweeping pencil beams 70 are formed by a tube 50 with apertures 56 (best seen in FIG. 4) that rotates through the fan beam created by the slot-collimator 10. Tube 50 is made of material opaque to the x-rays. The height of apertures 56 together with the width of slot 22 or 24 define the cross-section of pencil beam 70 that exits from the true focus scanner.

Figure 6:
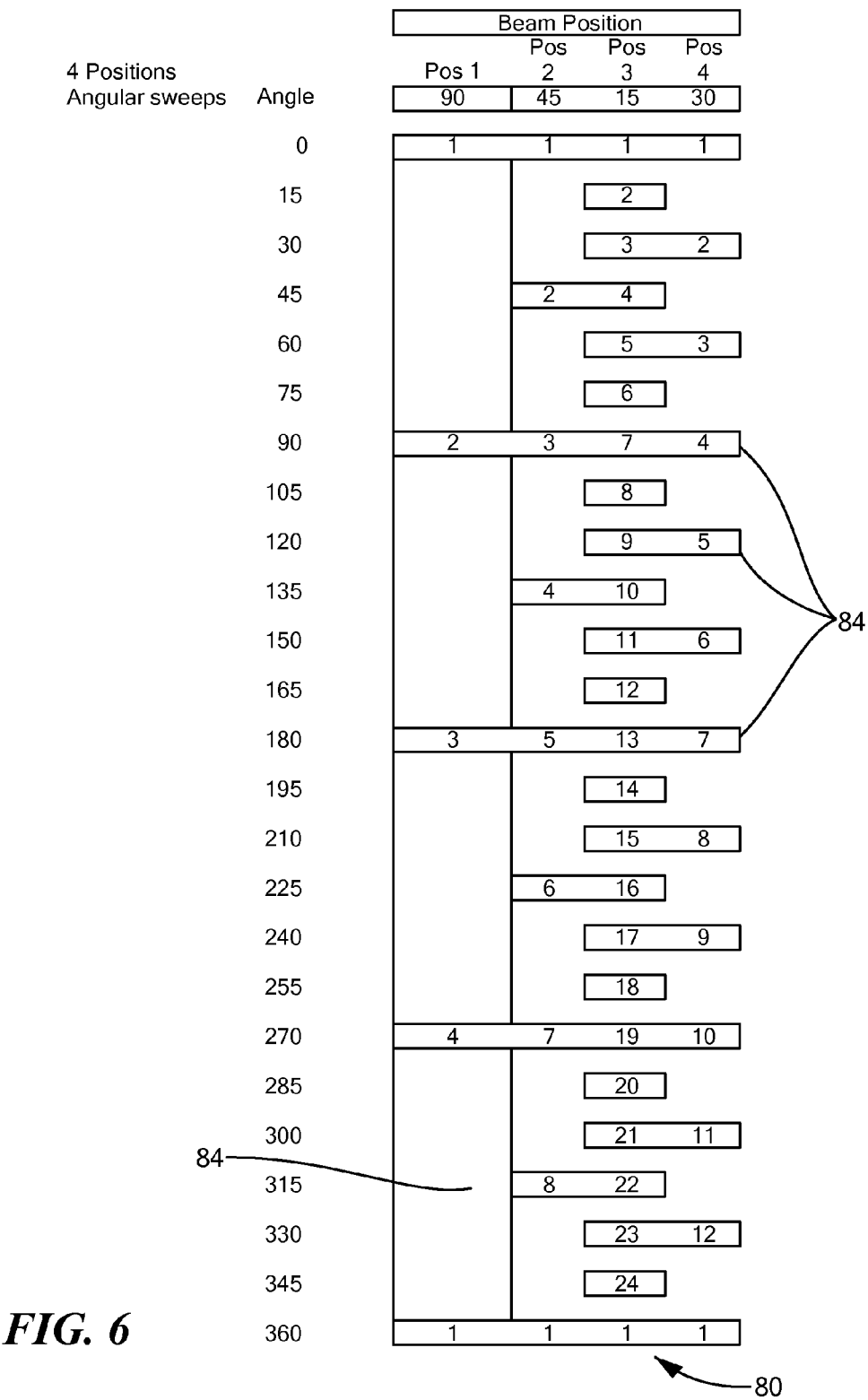
FIG. 6 shows a flattened depiction of the multi-slot aperture tube, more particularly showing an arrangement of slots to obtain 90°-, 45°-, 30°- or 15°-views, in accordance with a preferred embodiment of the present invention.

In the preferred embodiment of tube 50, the apertures are slots 56 rather than the traditional holes. Slots 56 are arranged in a pattern that is determined by the maximum scan angle and the number of smaller scan angles in the design. The total number of slot apertures is commensurate with 360°. The scan angles are also commensurate with 360°. FIG. 6 shows the pattern in a depiction in which the multi-aperture tube 50 is stretched out as a flat ribbon 80. The aperture slots 84 are dark gray horizontal bars, the beam position 88 is a light gray ribbon. The slots are arranged in the 4-choice example above: 90°, 45°, 30°, and 15°. Ribbon 80 has a four-fold repeat pattern of 6 slots, making a total of 24 slots along the circumference. The slots are arranged so that each of the 4 angular openings, 90°, 45°, 30° or 15°, can be placed in the beam 70 by moving the tube 50 laterally.

Variable Beam Scanner for Distant Targets.

The basic unit 2 (shown in FIG. 1) has applications for inspecting targets that are close enough to the beam-forming aperture for the scanning x-ray pencil beam to create a useful image. An x-ray inspection system, mounted inside a vehicle, and used, for example, to image targets outside the vehicle, requires, in practice, an additional beam forming aperture to usefully inspect targets outside the vehicle.

As a rule of thumb, with many exceptions, the beam-forming aperture 175 (in FIG. 7) should not be much further from the target than five times the distance from the x-ray tube's focal spot to the beam-forming aperture; the closer the better. The basic unit 2, shown in FIG. 1, can, in principle, be used for distant objects by making the diameter of the multi-aperture tube 50 as large as necessary. This approach can be useful for low-energy x-ray beams that can be effectively shielded by relatively light-weight hoops. For x-ray energies in the hundreds of keV, which require thick shields of high-Z material, a large radius results in a large rotational moment of inertia, which in turn limits the rotational speed of the beam scanner, and that in turn limits the speed with which the inspection unit can scan the target.

Figure 8:
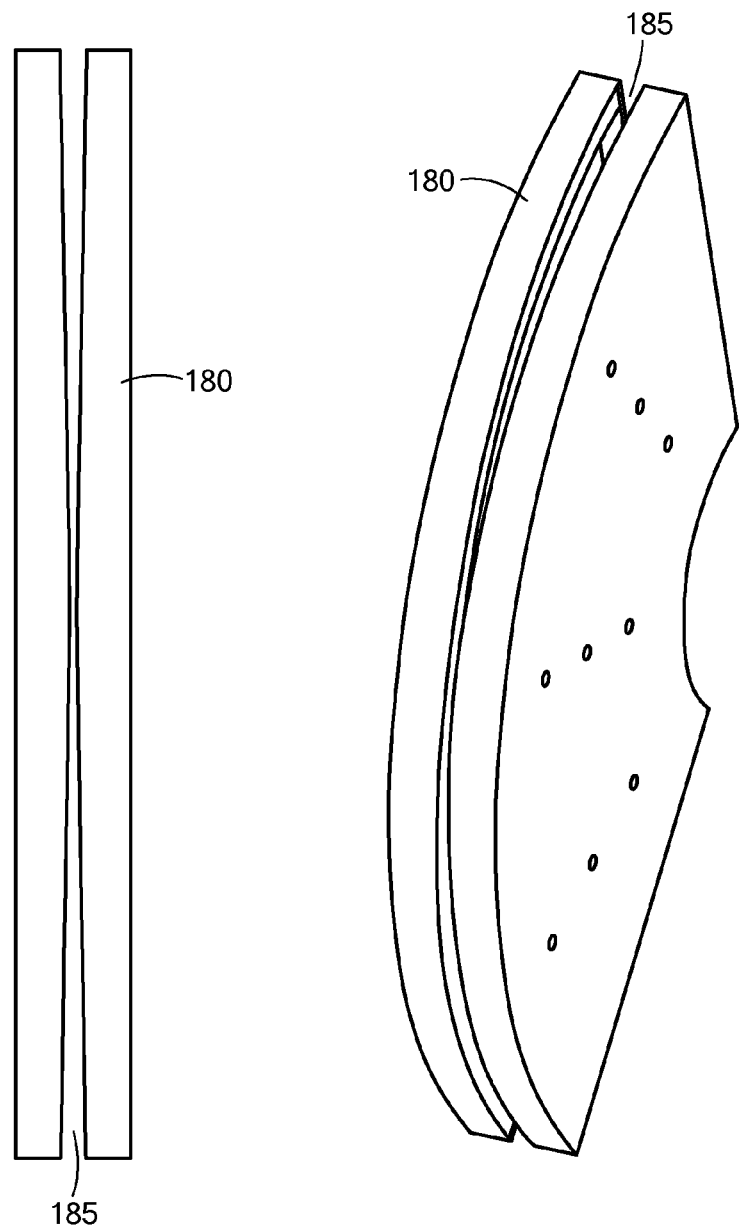
FIGS. 8A and 8B are front and perspective views of one embodiment of a collimator of the present invention.

The solution to the aforementioned difficulty is to use the multi-aperture tube 50, constructed of x-ray-opaque material, as an initial collimator and add a light-weight, rotating large-diameter outer loop 170, and another stationary collimator 180 of the beam width, to refine the cross section of the pencil beam. This concept is illustrated in FIGS. 7 and 8. Before describing these figures, the importance of this approach is further elaborated.

The rotational moment of inertia of a hoop is proportional to $MR^2$, where M is the mass of the hoop and R is its radius. The mass M required to effectively absorb an x-ray beam of a given energy is itself approximately proportional to the radius R since the thickness of the needed absorber is approximately independent of radius. Thus the rotational moment of inertia of the multi-aperture hoop is approximately proportional to the cube of the hoop's radius. Example: An 8" OD tube made of ½" thick tungsten has a rotational moment of inertia that is 25 times smaller that of a 24" OD tube made of ½" thick tungsten. (The thicknesses correspond to 20 mean free paths (mfp) of absorption at 180 keV, i.e. an attenuation of ~$10^9$.) Combining the smaller radius tungsten tube with an outer hoop made almost entirely of light-weight material results a significantly lower moment of inertia of the system, hence a higher maximum rotational speed.

FIG. 7 is an exploded view showing the elements of a preferred embodiment for distant targets. Each element is considered in turn. Basic unit 2 is the same as that shown in FIG. 1 except for the addition of an x-ray filter 150 in the form of a thin tube that surrounds x-ray tube 4. An empty slot in one quadrant of the filter tube 150 allows the full x-ray flux 8 to emerge. Filter tube 150 can be rotated so that different filters can intercept the fan beam to change the energy distribution or the deposited dose at the target. For example, a truck may be scanned with an automatically inserted filter 155 to reduce the dose when the passenger compartment is being scanned. The variable filter tube may be omitted if the application does not require changing the energy distribution of the x-ray beam.

The maximum opening angle of the scanning beam is defined by the slot collimator 14 with its discrete set of slots or the continuously variable slot 41 shown in FIGS. 3B-3E, whose angular width is controllable. As above, an inner aperture ring coarsely generates a square flying spot by passing a slot (up to 24 slots per revolution in the examples herein) across the fan-beam slit. After the beam passes out of the inner aperture ring 58, it travels in open air until it encounters a pair of jaws 180 that has an adjustable gap 185. These jaws (which may also be referred to as a "clamshell collimator") redefine the width of the beam and enable the final spot width to be adjusted if necessary or desired. A hoop 170 rotates in registration with the inner multi-aperture tube 58. The number of the equally-spaced apertures 175 in hoop 170 is equal to the largest number of apertures in the rings 58 of tube 50; in this example, there are 24 slots 175 spaced 15° apart. The length of the slots 175 is larger than the zero-degree slot width of tube 50; that is, the length is greater than any of the slots in the inner multi-aperture tube 50. The outer hoop 170 is preferably supported by duplex bearings on the far side. Various elements of the embodiment depicted in FIG. 7 are shown schematically in FIG. 10, for further clarity.

Figure 9:
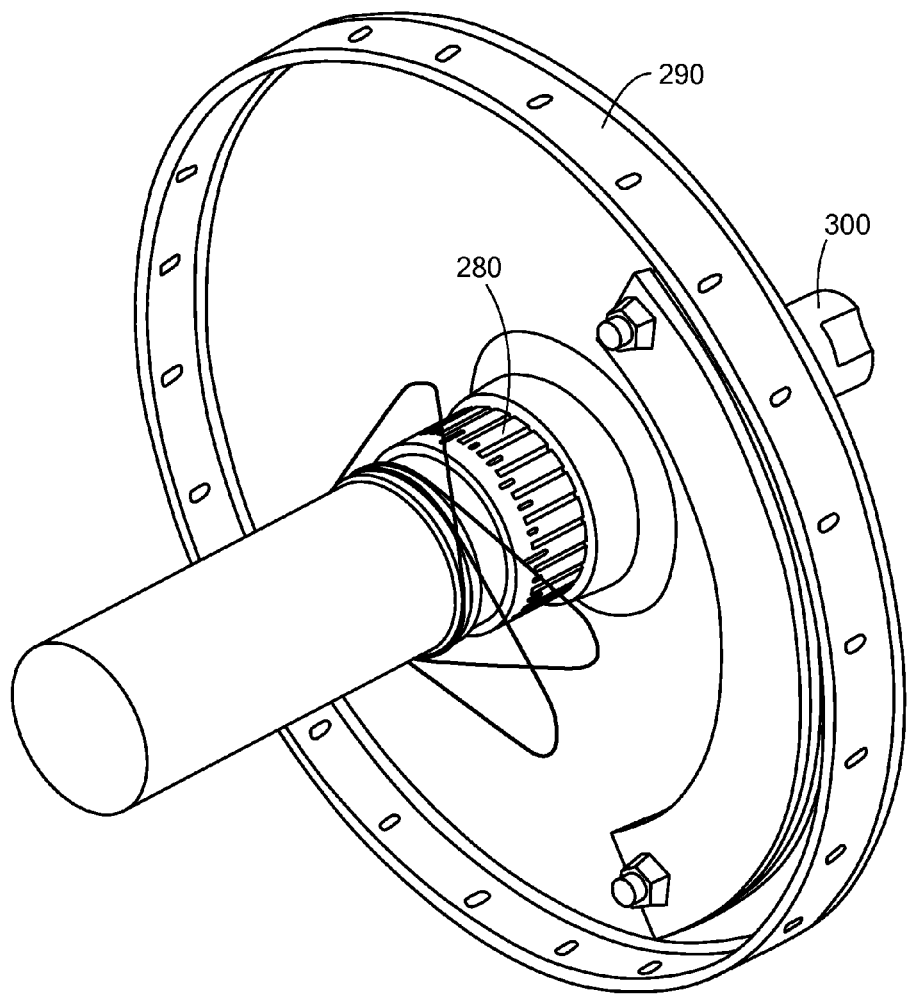
FIG. 9 shows an assembly view of a versatile beam scanner, in accordance with an embodiment of the present invention.
Figure 10A:
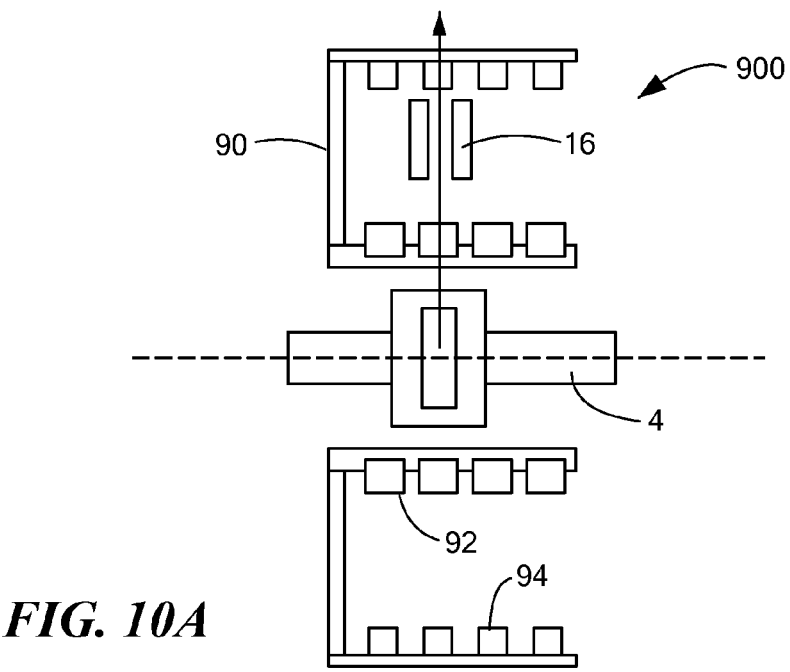
FIG. 10A is a cross-sectional depiction of an alternate embodiment of the invention in which the inner multi-slot tube and outer multi-slot tube are rigidly coupled to form a bundt-cake scanner, in accordance with an embodiment of the present invention.
Figure 10B:
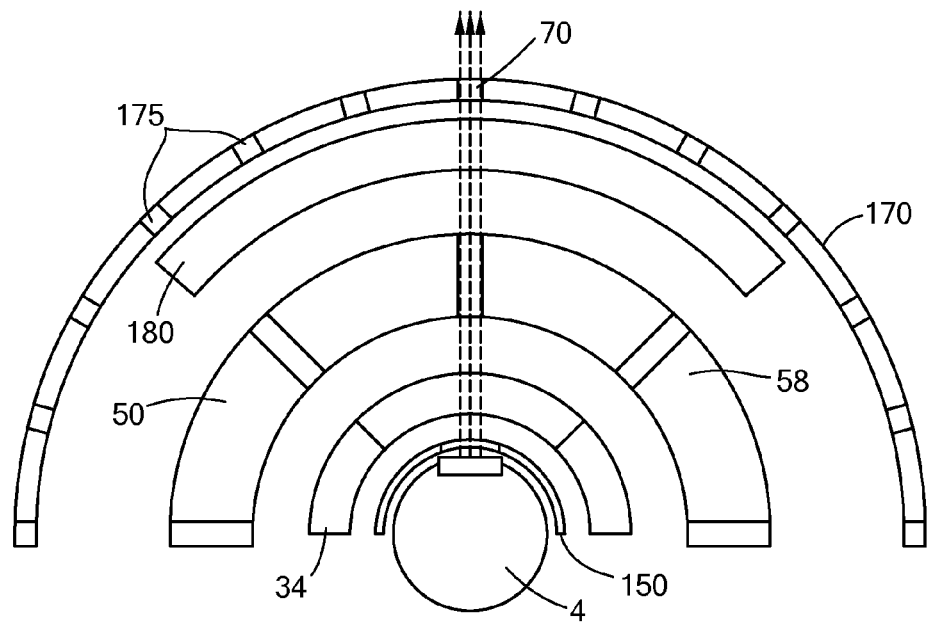
FIG. 10B shows a schematic view of elements of a versatile beam scanner, in accordance with the embodiment of the present invention depicted in FIG. 7.

One of various alternate embodiments of the present invention is now described with reference to FIG. 10A. In what might be referred to as a "bundt aperture system, designated generally by numeral 900, multi-aperture tube 280 and the multi-aperture hoop 290 (of FIG. 9) are a single unit 90. Inner apertures 92 and outer apertures 94 co-rotate about x-ray source 4. Adjustable jaws 16 may be disposed between the co-rotating sets of apertures. The bundt configuration, shown in an assembly view, may not have the versatility of the embodiment depicted in FIG. 7, and it may have a larger rotational moment of inertia, but it does have the mechanical advantage of simplicity in changing the sweeping angle, from say 90° to 15°, by step-wise translation of the bundt 90 and its drive motor, which is coupled to shaft 300 (shown in FIG. 7). Different scan angles are selected by translating the bundt scanner so as to register a selected plane of bundt slots with the plane of the fan beam. In accordance with yet another embodiment of the present invention, the bundt and drive motor may remain fixed while the rest of the unit is translated.

The embodiments described above are but a few of the permutations that embody the basic concept of an operator-controlled, multi-slot collimation coupled with a multi-aperture pencil-beam creator. For example, the three basic components—width collimator 14, angle collimator 34 and multi-aperture unit 50—can be permuted in any of the six possible configurations, the choice being made on the basis of application and mechanical design considerations. One alternate configuration would have the x-ray beam traversing unit 34 first, then unit 14 and finally unit 50. Another has the x-ray beam traverse the unit 50 first, then unit 14 and then unit 34.

It should be noted that among the variations that retain the fundamental concepts of zooming with variable beam resolution is the reliance of the variable angle collimator 34 to act also as the first width collimator, thus eliminating the separate width collimator 14. This simplification comes at a cost of some versatility (e.g. the number of opening angles are more restrictive) but may be useful for some applications, in particular when using the outer tube configurations of FIG. 7 or FIG. 10B in which the width of the beam at the target is controlled by the variable gap 180 in FIG. 7 or 16 in FIG. 10B.

Filter wheel 150 may provide a variable filter to change the radiation dose delivered to the target or to modify the energy distribution of the x-ray beam. Filters may also be incorporated in the slots of the variable angle tube 34 to place filters in the 45°, 30° and 15° slots that progressively increase the filtration of the lower energy components of the x-ray beam, to reduce the dose without significantly affecting the higher energy components of the x-ray beam. It should also be noted that filter wheel 150 may be omitted, for example, for applications in which the inspection is always carried out on inanimate objects.

In still another configuration, hoop 50 has a larger number of apertures such that multiple apertures are illuminated by fan beam 8, producing two pencil beams 70 that sweep in alternation through the target at different angles to obtain a stereoscopic view of the interior. This application uses a wide fan beam and an appropriate multi-aperture unit and slot collimators.

Improving an Image by Improving the Vertical Resolution of the Scanning Pencil Beam.

Figure 11A:
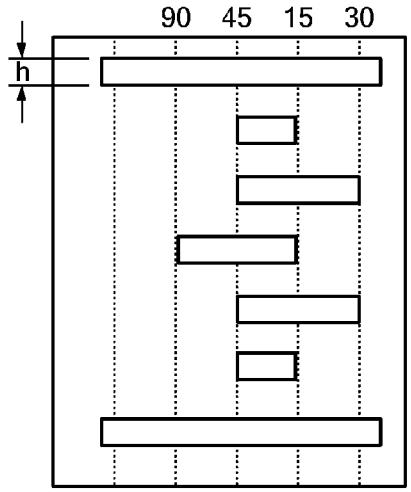
FIG. 11A shows a flattened depiction of the multi-slot aperture tube, with slots for 90°-, 45°-, 30°- or 15°-views, all slots of identical height, in accordance with an embodiment of the present invention.

In the discussion, supra, with reference to FIG. 7, slots 175 of rotating outer hoop 170 are all the same height, h, as depicted in FIG. 11A for one set of slots for the four different scan angles, 90°, 45°, 30° and 15°, in the example of a preferred embodiment. However, to change the height resolution, in accordance with alternate embodiments of the present invention, the slot heights in the outermost rotating aperture hoop must be changed, as illustrated by the following three examples.

Figure 11B:
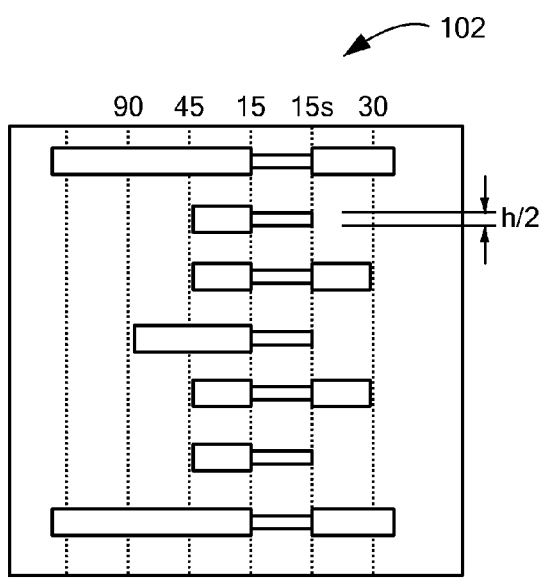
In FIG. 11B, an additional ring of half-height slots is added.

FIG. 11B shows an additional ring 102 of half-height slots added to the 15° ring of apertures. The operator can select either the 15° or the 15 s° lateral position; the latter reducing the height of the beam at the target by a factor of two. The width the slots in the aperture hoop has been increased by about 3 mm to accommodate the extra ring of apertures. In a preferred embodiment, 4 rings of apertures are maintained, but the heights of all the slots in the 15° ring are halved. This mode uses half of the six-fold gain in areal intensity of x-rays on the target, compared to the 90° view, to improve the vertical resolution by a factor of 2.

In another embodiment of the invention, rings of apertures of different heights are added to the 90° viewing angle. That allows automated changes in height resolution as a function of the target distance. A target passing at a distance of 5 ft. might be most appropriately scanned with the aperture ring that has 1-mm slot heights, while a target passing at 3 feet might be more appropriately scanned with a 0.5-mm resolution. It should be clear that, within the practical constraints of weight and size, more than one of the above examples can be accommodated on a single rotating hoop.

Two Independent Views with Different Vertical Resolutions.

Figure 11C:
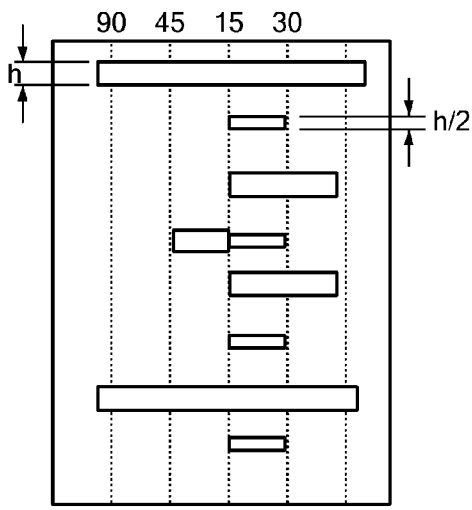
FIG. 11C shows a slot pattern for obtaining two separate 15° views, both in accordance with other embodiments of the present invention.

Embodiments of the present invention may also be used to simultaneously obtain two (or more) images each with its own vertical resolution. FIG. 11C shows a slot pattern for obtaining two separate 15° views. Alternate 15° sweeps form one image with a vertical resolution h, and another image with a vertical resolution h/2, or smaller. Improved spatial resolution can be essential for resolving issues of interpretation in the image.

Dual Energy.

In other embodiments of the present invention, filters may be placed in all, or in a subset of, the slots of one of the arrays of slots, with either the same or different vertical heights, to change the x-ray energy distribution impinging on the target. In the slot configuration of FIG. 11C, a filter in the alternate slots of the 15° scan can produce a separate view that minimizes the lower-energies that inspect the target and thus enhances the image of deeper penetrating radiation. If all the slots in the 15° scan have the same height, a filter placed in alternate slots may yield new information, including material identification, when the filtered image is compared with the unfiltered energy image.

The two-view or dual-energy modes are achieved to particular advantage in accordance with the present invention. The aperture hoop 170, rotating at the nominal speed of 3600 rpm, makes a 15° scan every 680 microseconds. A target vehicle, moving at the nominal speed of 5 kph, travels ~1 mm during that scan, which is much smaller than the beam size at the nominal target distance of 5 feet. As a consequence, the two views will be within 10% of overlap registration. The above calculation indicates that even when no provision is made to change the height of the pencil beam, the slots in the beam-resolution defining hoop should not have the same heights. The correct heights will depend on the application.

Horizontal Resolution.

For distant targets, where two concentric rotating hoops (50 and 170) of apertures are employed, the horizontal resolution is determined by the slit width 185 of the outer slot collimator 180. The plates that form the width collimator are controlled by servo-motors. In a preferred embodiment, the width collimator is in the form of a clamshell whose jaw opening is controlled by a single motor near the clamshell's hinge. The width may be controlled by the operator or may be automatically changed as a function, for example, of the relative speed of the inspection vehicle and the target. For inspection of close targets it may not be useful or desirable to use the outer hoop 170 and the outer slit 125. In that case the horizontal resolution would normally be controlled by changing the width of the 90° slot 24 of the inner tube 14, though other methods will be apparent to those familiar with mechanical design. The width of slot 24 for the preferred embodiments is nominally 2 mm wide or less, though any slot width falls within the scope of the present invention.

Offset Hoop.

U.S. Provisional Application Ser. No. 61/533,407 introduces the concept of backscatter x-ray inspection (BX) by a scanning pencil beam of x-rays produced by an electron beam whose the axis is offset from the axis of rotation of a rotating ring of apertures that forms the scanning beam. Offsetting a source behind the axis of rotation of an aperture hoop had been known. The novel forward-offset concept has inherent advantages, as in the application of x-ray inspection portals, where its effectiveness for faster scanning at close geometries allows a greater throughput of inspected vehicles. In accordance with embodiments of the present invention, components of angle selection and variable-beam resolution are added to forward offset scanning to significantly increase the system's versatility.

In one embodiment of the present invention, a forward-offset portal system that inspects vehicles from both sides and the top, can, on the fly, change the angle rate of scan per revolution, as well as the scan resolution and the radiation exposure, to optimally inspect either trucks or cars. An effective portal inspection system of cars and trucks may use the x-ray backscatter technique (BX) to scan from both sides and from the top, as the vehicles pass through. The x-ray beams from the three BX systems are interleaved to prevent cross talk. That requirement places a severe limitation on the speed of the inspected vehicles. For example, a standard one-sided BX system that uses a 3-spoke aperture hoop, when applied to a three-sided inspection, limits the truck speed to less than 4 kph. To overcome this limitation, U.S. Provisional Application 61/533,407 teaches offsetting the x-ray tube axis forward of the axis of the aperture hoop that forms the pencil beams. The forward offset concept allows wide-angle scans of trucks with a six-aperture hoop, and a nine- or even a 12-aperture hoop for scanning smaller vehicles.

Figure 12:
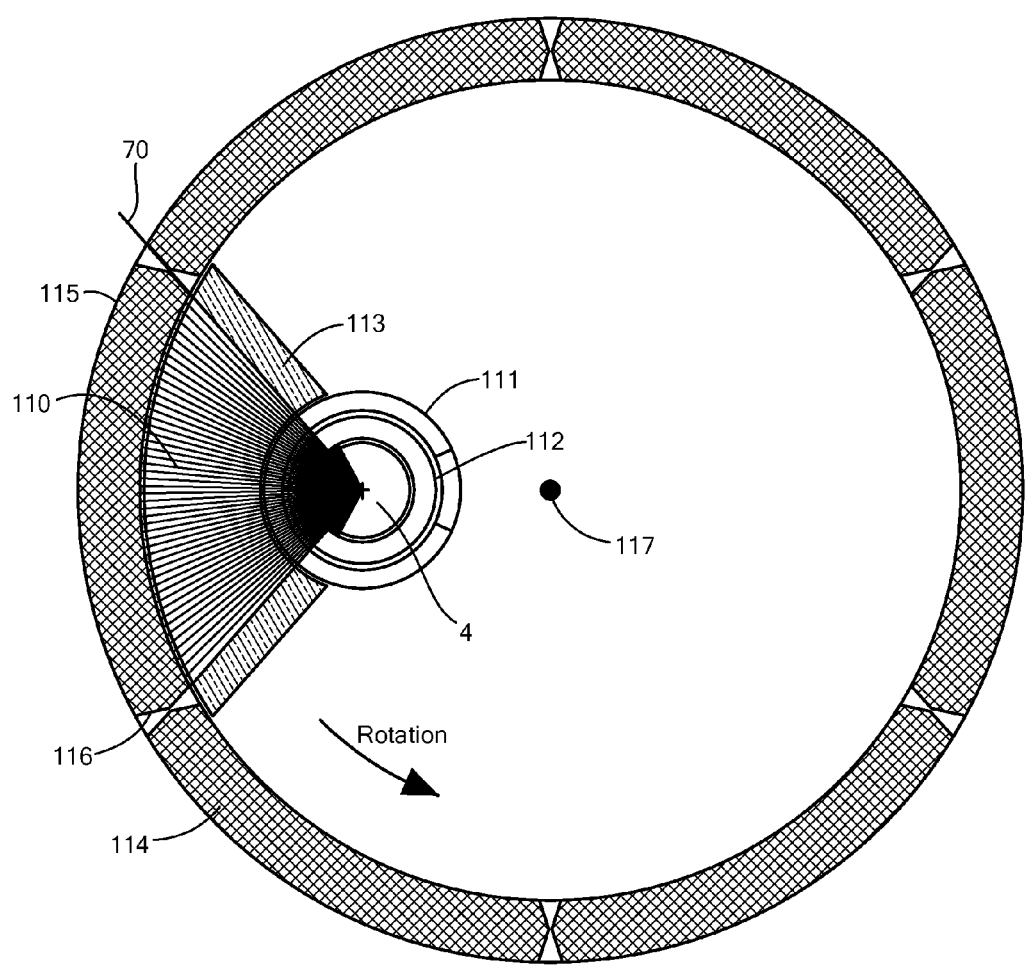
FIG. 12 is a schematic cross-sectional depiction of a versatile beam scanner, in accordance with the present invention, with an x-ray tube in a forward offset position.

To increase the versatility of the forward offset concept, embodiments of the present invention in which the axes of the x-ray tube 4 and of the hoop 114 of rotating apertures coincide, as now described with reference to FIG. 12. The scan angle of fan beam 110 is defined by an angle selecting ring 111 that may be a variable slot or a ring with two or more fixed slots. The outer hoop 114 contains the beam-forming rings of apertures 115, each ring of apertures matches a given selected scan angle. A wide-angle collimator 113 confines the beam from the angle selector 111 to a single ring 115 of apertures. To co-plane the beam 110 from the angle selector with the appropriate ring of apertures, the x-ray tube 4 plus angle selector 111 plus collimator 113 are on a movable positioning platform (not shown), which serves to move those elements in a direction into the plane depicted in the cross-sectional view. The system may include the following components:

a. an x-ray tube 4, well-shielded by a tube shield 112, where the x-ray tube is offset from the center of a rotating hoop, and produces a fan beam 110 of x-rays that emanates approximately perpendicular to the x-ray tube's beam axis.

b. a rotatable angle-selector ring 111, with a variable angular slot or with selectable angular slots, is coaxial with x-ray tube 4. The ring 111, typically made predominately of lead, is impenetrable to the x-rays except for the slots that define the scan angles available for inspection. To optimize the scanning of both trucks and cars, there may be two or more slots to accommodate the different heights of trucks, SUVs and cars. The closed position of the angle-selector ring, which is the default position when the power is off, is the x-ray shutter for the system.

c. an outer hoop 114, made of material that effectively blocks all x-rays except for those that pass through equally-spaced apertures 116, forms the pencil beams 70 of x-rays. The rotational axis of the hoop 117 is offset from the axis of the x-ray tube 4 by a distance D (shown in FIG. 12). The apertures may be arranged in separate rings. The number of apertures in a given ring must be commensurate with 360°; e.g. six apertures spaced 60° apart. Each ring of apertures corresponds to one of the opening angles in the angle-selector ring.

d. a collimator (typically, a clamshell collimator) 180 (shown in FIGS. 7 and 8A-8B) between the collimator ring and the outer hoop co-planes the fan beam to the appropriate ring of apertures for the selected angular scan. The azimuthal opening of the collimator is fixed to accommodate the widest scan angle. The axial opening angle of the collimator controls the x-ray beam's axial resolution as well as the radiation dose on the target.

A separate filter ring 150, coaxial with the x-ray tube, with angular segments of different absorbers to filter the x-ray beam either to control the flux on the target and/or to control the energy spectrum of the x-rays on the target.

X-ray tube 4, angle selector 111 and clamshell collimator 180 are mounted on a platform that moves, under motor control, to place the fan beam plane in the plane of the aperture ring appropriate for the selected angle. It should be noted that in some applications the rotating outer hoop translates, the other components are stationary.

One of the innovations in this invention is the use of rectangular slots instead of round or oval holes for purposes of chopping a beam. As used herein, the terms "slot," "aperture," and "through-hole" may be used interchangeably. The chopped beam may be a beam of particles having mass or of massless particles, including electromagnetic radiation over a specified wavelength range. In accordance with various embodiments of the present invention, a chopper, such as aperture wheel 170 (shown in FIG. 10B), interrupts a beam of particles 70 characterized by a propagation direction. The chopper has a solid portion, which is an obscuring element substantially opaque to passage of the particles in the propagation direction. Aperture wheel 170 has one or more through-holes 175 (shown in FIG. 10B) in the obscuring element adapted for passage through the obscuring element of particles in the propagation direction. Aperture wheel 170 is spun by an actuator (not shown to interpose the through-holes 175 in the beam on a periodic basis.

The innovation of rectangular chopper apertures has two independent advantages over traditional round or oval apertures. First, is its usefulness in a single ring of apertures. The size of the pencil beam determines its spatial resolution or point spread function. Oval or circular apertures result in fixed resolutions that are difficult to change precisely. Slot apertures have fixed angular widths but variable axial lengths (dimension parallel to the beam axis) controlled by the clamshell collimator opening. The size of the beam spot can be precisely controlled by the collimator opening and the integration time of the pixel. The second advantage is evident when the outer aperture hoop has two or more rings of apertures, i.e., zooming ability, each ring with a different number of apertures. Round or oval apertures strongly limit the ability to vary the size of the pencil beams. The use of slots, as exemplified in FIGS. 11A-11C, has both advantages of manufacturability and greater range of the axial width for a given length of slot.

The azimuthal widths of the slots are typically the same across all the slots, but the slot lengths (parallel to the x-ray tube axis) preferably have a pattern that is determined by the opening angles of angle-selector ring 111. In a 3-angle selector ring, for example, one ring has 3 apertures spaced 120° apart; an adjacent ring has 6 apertures spaced 60° apart; a third adjacent ring has 9 apertures spaced 40° apart. The pattern of slots is: 3 long slots at 0°, 120°, and 240° for the scan angles that are common to the 3 modes, and 12 short slots for scan angles that are unique to their mode. The slotted pattern has the significant advantage over round or oval apertures that the axial extent of the beams can be quantitatively adjusted by the clamshell collimator to change the beam resolution and/or adjust the radiation dose.

In addition to rectangular through-holes, a chopper in accordance with embodiments of the present invention may also have biconical ("hourglass") or conical through-holes, as shown, respectively, in FIGS. 17A-17B, and 17C-17D, respectively. Such shapes advantageously serve to maximize beam throughput in the face of lateral beam offset. In embodiments employing more than one ring of apertures, each ring of apertures should have its own unique conical angles. Slotted apertures preferably have different slopes along the slots.

The offset scanner concept described herein may be applied advantageously to both forward and backward offsets. For heuristic reasons, the offset scanner is describe herein primarily in terms of an offset in the forward direction (i.e., toward the target, as might be employed in portal systems for inspecting large and small vehicles, however it is to be understood that the relative position of the tube axis and hoop axis does not limit the scope of the invention as claimed.

Figure 13:
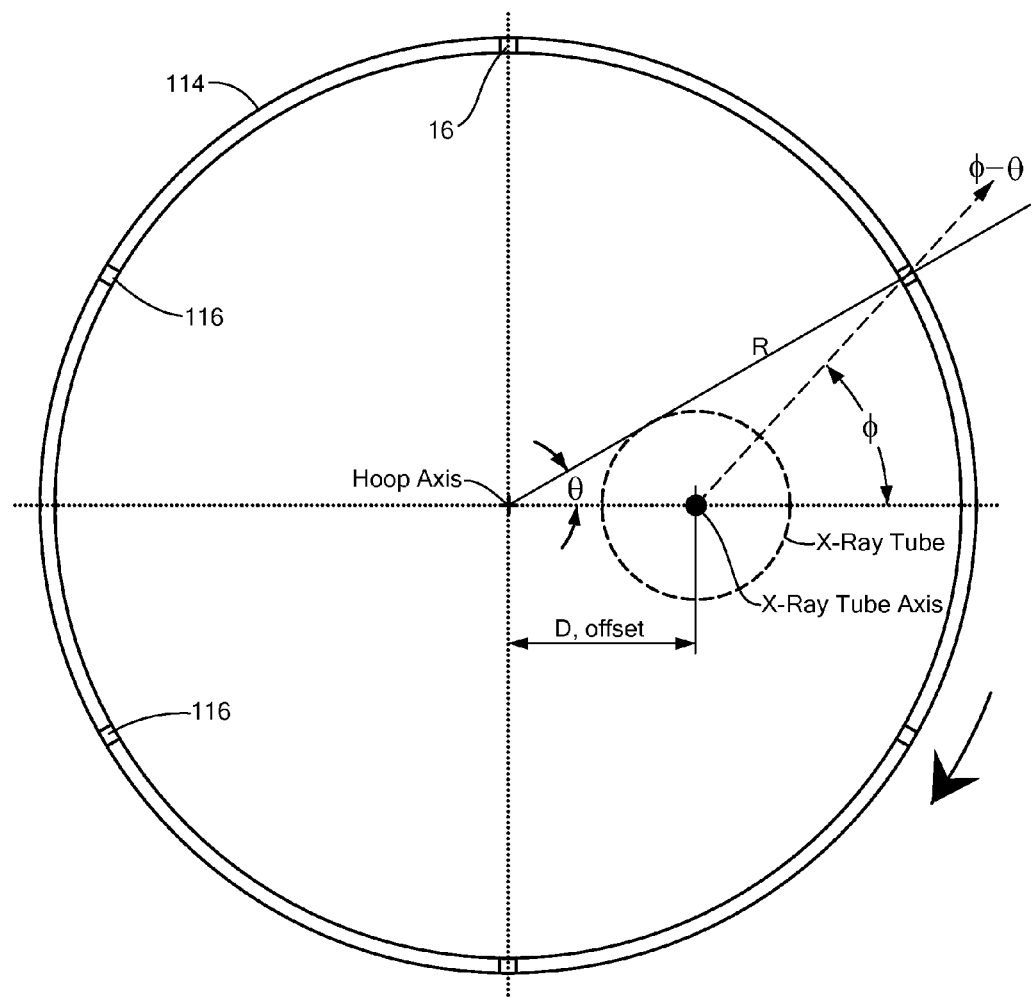
FIG. 13 depicts the geometry of a rotating aperture hoop with an axis offset with respect to an x-ray tube, in accordance with embodiments of the present invention.

FIG. 13 is a schematic drawing depicting the geometry of the system. The tube is forward-offset by a distance D from the axis of the hoop of radius R. The fan beam exits to the right; the center of the fan is at 0°. Apertures 116 along the rim are equally spaced, i.e., commensurate with 360°. Six apertures, spaced 60° apart are shown in FIG. 13. Aperture 1 is at an angle θ with respect to the hoop axis, and an angle ϕ with respect to the tube axis; ϕ>θ. The relationship between ϕ, θ, R and D is given by:

$$\tan\phi = \frac{\sin\theta}{\cos\theta - \frac{D}{R}}. \tag{1}$$

In the case of a backward offset, D/R is added to cos θ in the denominator rather than subtracted.

Figure 14:
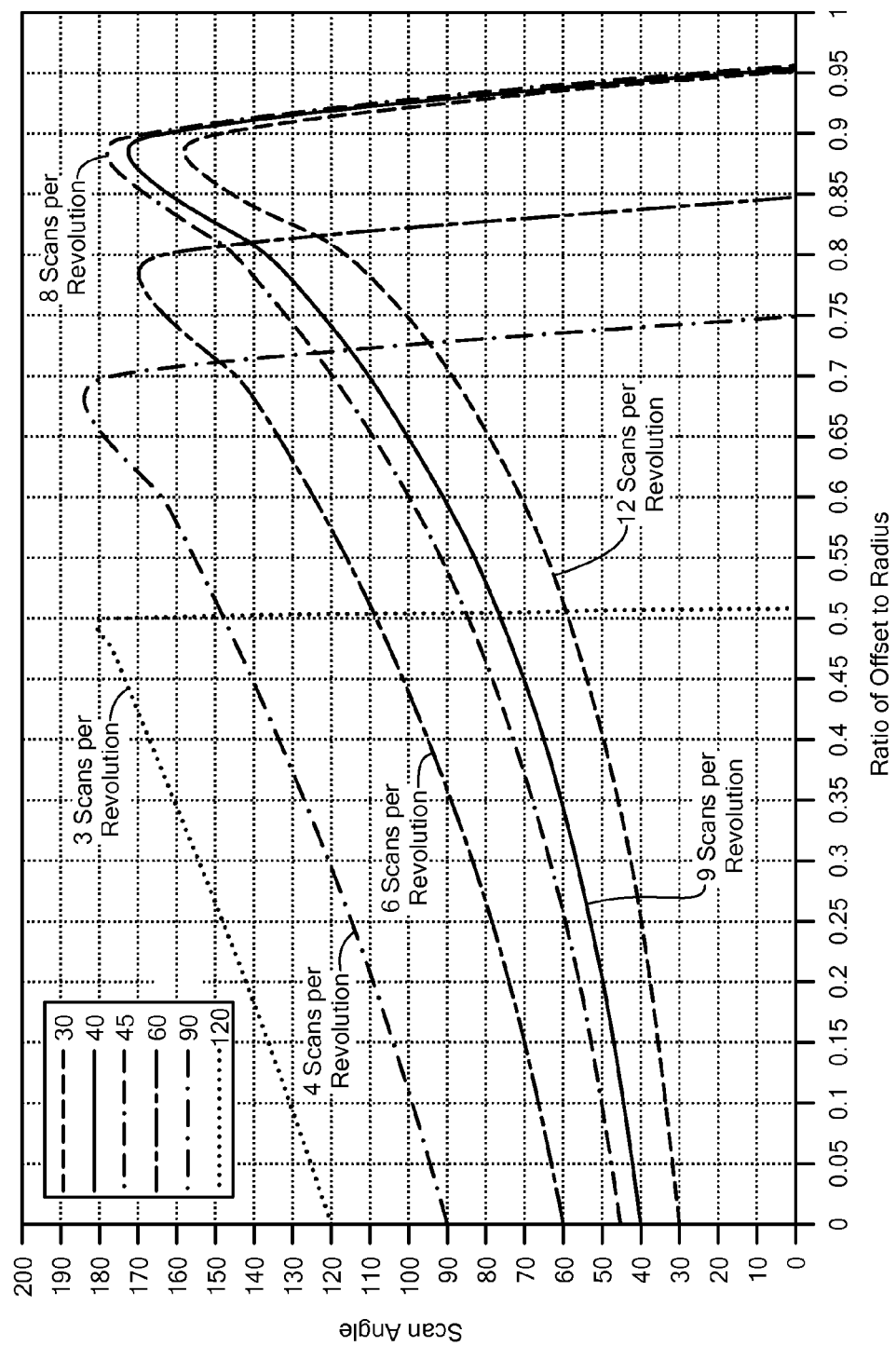
FIG. 14 plots the dependence of the fan-beam angle, $2\phi$, on the ratio D/R, for forward and backward values of D, in accordance with embodiments of the present invention.

FIG. 14 is a graph of the scan angle (or, equivalently, opening angle, 2ϕ)), as a function of the ratio of the forward offset D to the radius R, for 3, 4, 6, 8, 9, and 12 scans per revolution (s/r) of the aperture tube. The number of scans per revolution (or, s/r values) are determined by the angular spacings, 2θ, between apertures, which are 120°, 90°, 60°, 45°, 40° and 30° respectively. For large values of D/R, ϕ can become negative, i.e., unphysical. (There are no unphysical values of D/R for backward offsets.) Within obvious constraints, the offset of the axis of x-ray tube with respect to the axis of the rotating outer hoop can be any direction and can have a wide range of values, including zero.

FIG. 14 shows the scan angles obtainable for aperture rings of 3, 4, 6, 9 and 12 apertures. A single revolution of the wheel allows the flux to scan 12 times over an angular range of 90 degrees (D/R=0.7), for example. That spreads the flux over 1080 degrees of scan. At 6 times per revolution of 120 degrees spreads the flux over 720 degrees of scan in one revolution. This feature, by itself, is a potent tool for reducing undersampling. Undersampling is an inevitable bottleneck to increasing maximum vehicle speeds to increase throughput. Until now, higher rotational speeds have been sought in order to achieve higher throughput, however the present invention advantageously provides requisite additional flux.

In principle, different D/R values can be used in a single scanning system. In practice, however, the D/R value is typically fixed. That still gives the system considerable flexibility to utilize all the x-ray beam flux in the x-ray beams on the target; i.e., to obtain maximum utilization of the flux. The following examples illustrate.

Example 1

A Portal System that Uses BX to Scan Cars, SUVs and Trucks from Both Sides, but not from the Top The fan beam from the x-ray tube is collimated to have an azimuthal extent of 120° and an axial width of ~2°. The x-ray tube is forward offset 24 cm from the center of a 60 cm diameter hoop (D/R=0.4). When trucks are inspected, the 4-aperture ring is selected and the beam opening angle selector is set at 120°. (A 120° beam is presently the practical limit for available x-ray tubes.) When cars/SUVs are inspected, the 8-aperture ring, and 72° slot are selected. The interleaving requirement results in 2 scans per revolution from each side of a truck and 4 scans per revolution from each side of a car.

Example 2

A Portal System in which Cars/SUVs as Well as Trucks are Scanned by BX Systems from Both Sides and from the Top.

The x-ray tube is forward offset 36 cm from the center of a 60 cm diameter hoop (D/R=0.6). FIG. 14 shows that a 124° scan can be obtained 6 times per revolution and a 70° scan can be obtained 12 times per revolution of the aperture ring. The 124° is effective for scanning sides of trucks while the 70° scan is sufficient for scanning through the top of trucks, and sufficient for use from every side of cars and SUVs. Cars can be scanned 4 times per revolution from all three sides. Trucks can be scanned 2 times per revolution from the sides and 4 times per revolution from the top.

Example 3

Accommodating Higher Vehicle Speeds and Hence Greater Throughput

An aperture hoop rotating at 3,000 rpm makes one revolution in 0.02 seconds. During that time, a vehicle traveling at 12 kph moves 66 mm The resulting under-sampling with one scan per revolution of an acceptable beam resolution results in unacceptable inspections at 12 kph, and speeds through present three-side portal inspections are limited to ~4 kph because they use only one sweep per revolution from each side, Examples 1 and 2 above show that forward offset allows trucks to be scanned twice as rapidly from the sides and 4 times as rapidly from the top Cars can be scanned 4 times per revolution from every side. These additional scans per revolution of the beam-forming wheel, together with an adjustable beam width by means of the clamshell collimator, allows trucks to be effectively inspected at 12 kph, and cars inspected at still higher speeds.

In accordance with various embodiments of the invention, rings of individual round or oval apertures may be used. Slots, however, when used with the clamshell collimator, are preferable, especially when multiple rings are used. FIG. 6 shows the pattern of 12 slots for Example 2 above. 6 of the slots, as 0°, 60°, 120, 180°, 240 and 300° are double width slots, while 6 slots at 30°, 90°, 150°, and 210°, 270° and 330° are single width slots. Either the 6-aperture ring or the 12 aperture ring can be selected; the 12 aperture ring is depicted in the figure. The clamshell collimator can change the aperture width from fully closed to 5 mm wide in that example, to cover a wide range of beam sizes and delivered dose.

Rotation of the X-Ray Tube.

In accordance with further embodiments of the present invention, provision is made for rotation of x-ray tube 4 about its axis 6 (shown in FIG. 1). Rotatability of the x-ray tube may advantageously increase the angular volume subject to inspection by the system, and may additionally be used to improve the beam resolution, as now described with reference to FIGS. 15A-15C, and 16.

Figure 16:
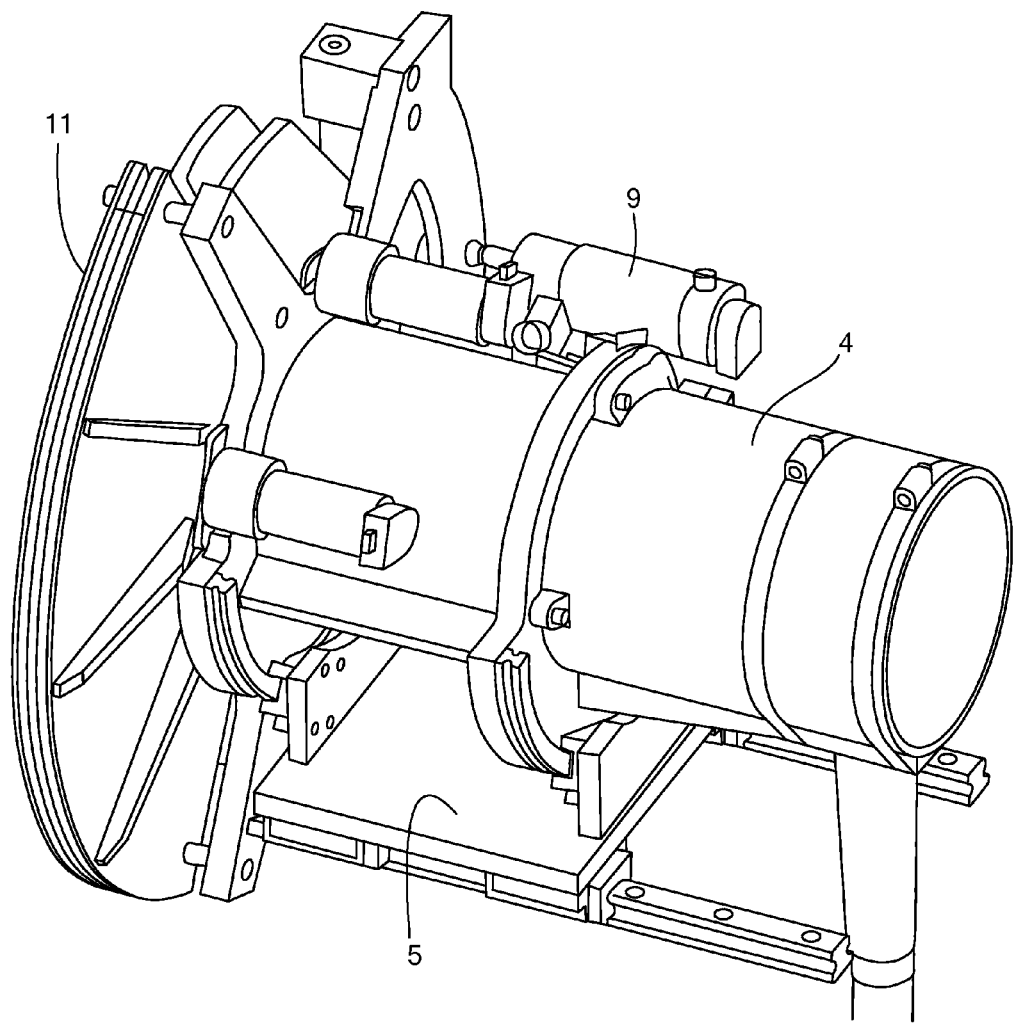
FIG. 16 is a perspective view of a rotatable basic unit including a rotatable x-ray source, in accordance with embodiments of the present invention.
Figure 17A:
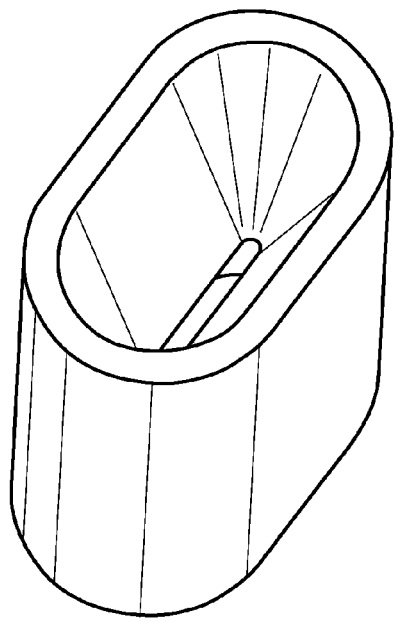
Figure 17C:
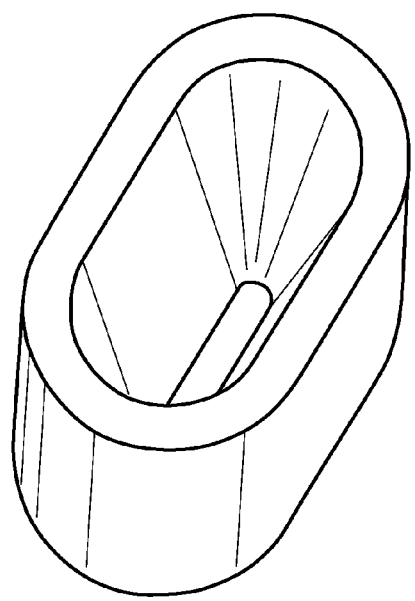
FIGS. 17C and 17D are perspective and cross-sectional views, respectively, of a conical aperture (or through-hole) for beam chopping, in accordance with another embodiment of the present invention
Figure 17B:
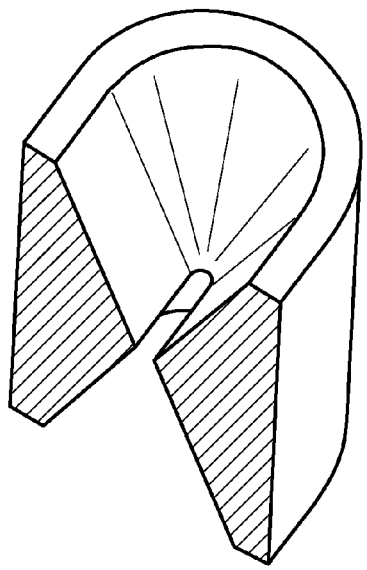
Figure 17D:
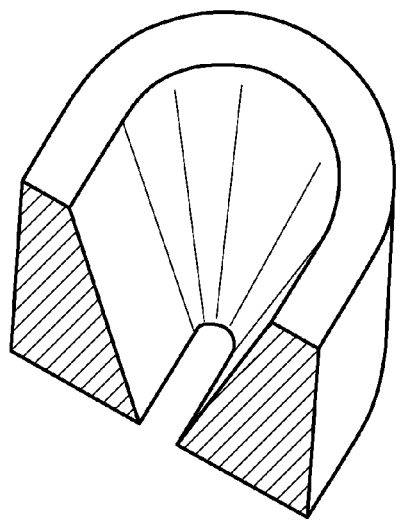

As shown in the perspective view of FIG. 16, x-ray tube 4 together with the angle selector 113, filter ring 150, and clamshell collimator 180 are rotatably mounted on a platform 5 that moves linearly to co-plane the selected fan beam with the appropriate ring of apertures. The fan beam 8 with an angular extent 15, typically provided by the tube's manufacturer, constrains the ability to change the usable direction and extent of that beam. For example, in the standard configuration in which the 120° fan beam from the x-ray tube is emitted horizontally, the basic scanning apparatus 2 can only manipulate the x-ray beam within that space. Advantages of a rotatable platform to versatile scanning systems in accordance with the present invention are now described.

An important application of the rotatable platform is to increase the angular range of backscatter inspection. For example, the maximum height that can be inspected in conventional portal systems using a 120° fan beams is about 14 feet. Higher vehicles cannot be fully inspected. The addition of a rotatable platform corrects that problem, allowing a second inspection of the top portion of a vehicle or targets that are 20 feet high or more.

Figure 15A:
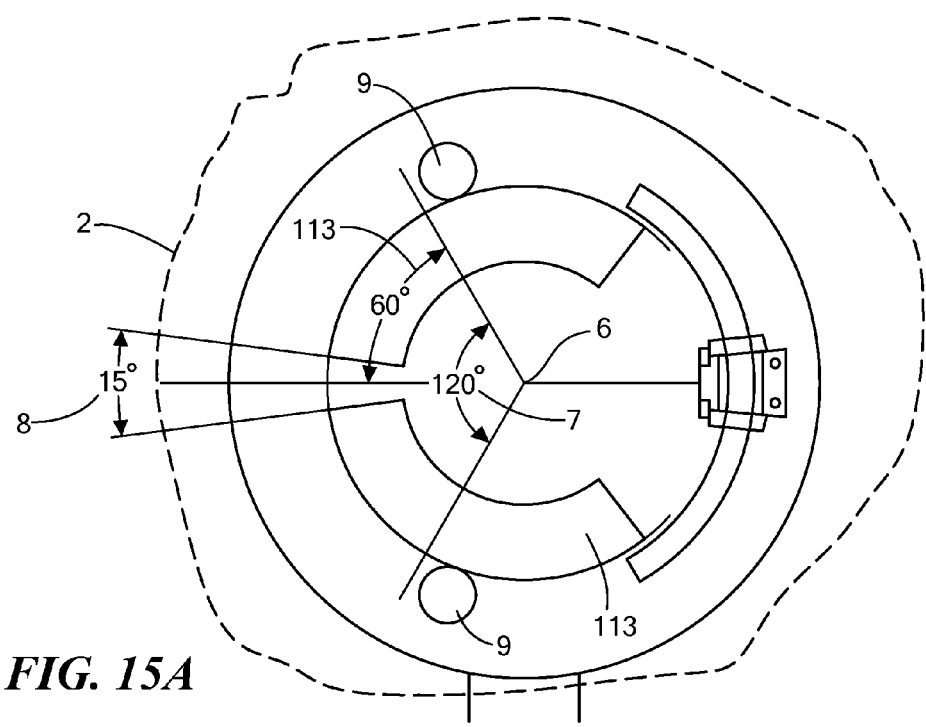
FIG. 15A-C are schematic cross-sections of an embodiment of the invention in which an x-ray source may be rotated, from a horizontal-pointing orientation in FIG. 14A to an orientation depressed by 52.5° shown in FIGS. 14B and 14C.
Figure 15B:
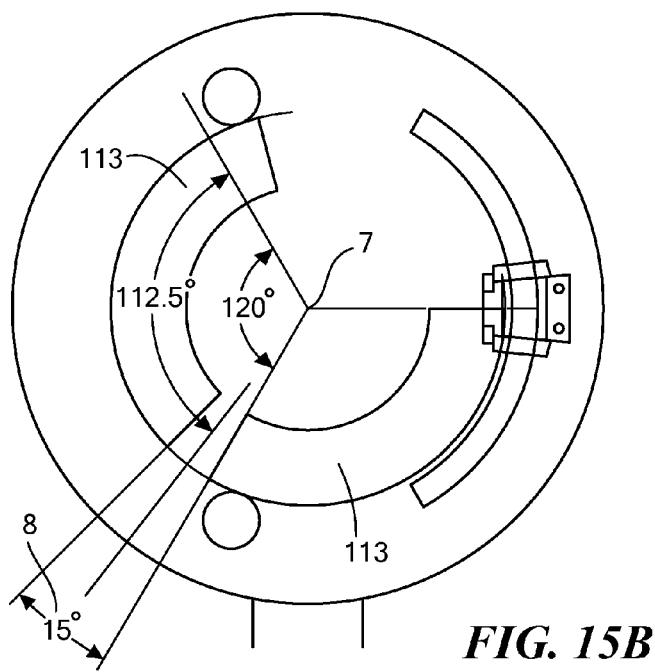
Figure 15C:
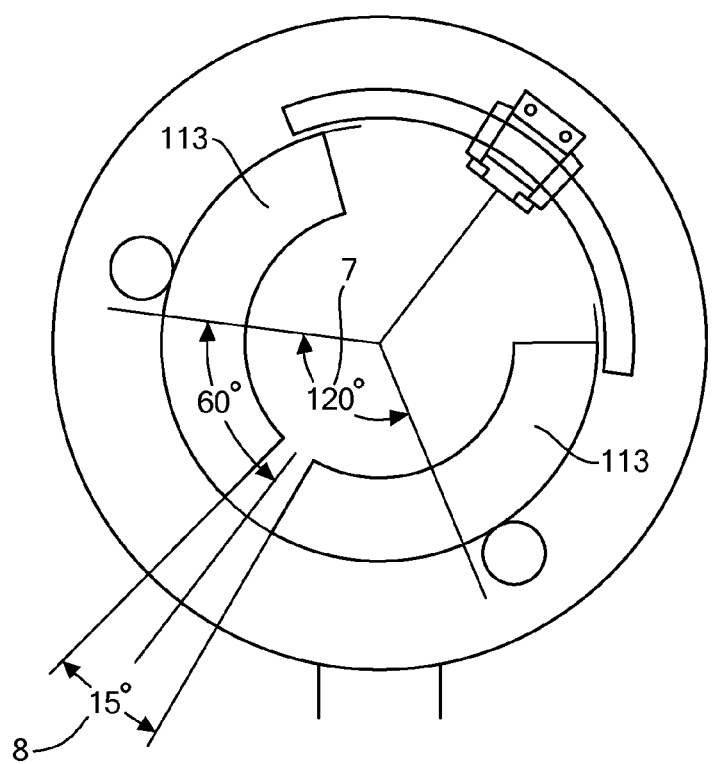

Another important application is to improve the spatial resolution of a secondary inspection of a small area of a vehicle. For example, a suspect area, found in a 120° scan, can be closely inspected by zooming into the suspect area with a 15° scan. The nine-fold gain in flux density will significantly improve the image of a suspect area. If, however, the suspect region is in the outer reaches of the 120° fan beam from the x-ray tube, the spatial resolution of the beam will be far from optimum and the full advantage of the zoom will not be realized. The resolution can be improved substantially by rotating the platform so that the axial ray of the scanning beam is centered on the suspect region. The sequence of steps is shown schematically in FIG. 15A to 15C, for a suspect region at the extreme of a 120° scan. In FIG. 15A, the 15° scan, defined by the scan-angle selector 113, is centered on the beam axis of the 120° fan beam 7 from the tube. The pencil beam emanates from a small, symmetric focal spot and the quality of the pencil beam is the best it can be for that x-ray tube. Without a rotatable platform, the suspect area is inspected with a 15° scan by rotating the two arms of the scan-angle selector 113 counter-clockwise 52.5°, using actuators 9, to the configuration shown in FIG. 15B. The quality of the pencil beams, however, has worsened because the effective focal spot has grown substantially. FIG. 15C shows the same geometry for a 15° scan of the suspect area, now formed by rotating the platform counter-clockwise 52.5° the beam axis from the x-ray tube is along the center of the 15° scan, and the beam quality has been optimized.

Improvement in resolution due to centering the inspected object in the x-ray tube emission beam can be further understood as follows. The spatial resolution of the backscatter image is determined by the cross-section of the x-ray beam, and that size is restricted by the focal spot size of the electrons on the anode. The typical x-ray tube (operated in a reflection configuration) focuses a line source of electrons (from a coil filament) as a line onto the anode, which is tilted with respect to the electron beam. The effective size of the focal spot depends on the viewing angle. For example, a line source of x-rays from an anode, tilted 15° with respect to the electron beam, is 1 mm high by 4 mm. The line source of electrons spreads the heat load on the anode, allowing for higher power dissipation and hence higher x-ray flux. The focal spot size of commercial x-ray tubes is specified only for the axial ray direction; in this example, the width of the focal spot is 1 mm and the effective height is also ~1 mm. The focal spot size at the extreme of a 120° fan beam, however, is a line source 1 mm wide by 4×sin 60°=3.5 mm long. Moreover, the beam quality is further diminished by the increased absorption of the x-rays in the anode itself, the so-called heel effect. Rotating the axial ray from the x-ray tube into the center of the zoom angle effectively eliminates both these effects.

Degradation of resolution with angular displacement from the center of the scan constrains the acceptable angular spread of the scanning pencil beam. Given that constraint, it is nonetheless often important to obtain the best spatial resolution for inspecting a specific target area that is not close to the central axis. To solve this problem the x-ray tube may be rotated together with the beam collimation so that the central axis of the x-ray beam is pointing in the direction of the desired target area.

Operator and Automated Features.

It is to be understood that the focusing operation may be performed by an operator, on the basis of an indicated suspect area that constitutes a portion of the inspected object. The angular opening of the scan, the direction of the scan, the beam's spatial resolution, and the number of scans per revolution can each or in combination be changed by the operator or by automation on the basis of the target height, and target distance from the beam chopper assembly, and relative speed of the target with respect to the assembly. The identical apparatus may thus advantageously be employed for performing a primary rapid scan, followed by a secondary, high-resolution, small-area scan of a suspect area found in a first, rapid scan.

For illustration, the operator may focus on a small, suspect area of a target that has first been scanned with a broad beam. A 3-aperture ring with apertures may produce a 120° wide scan of a large vehicle. The collimators of the angle selector may then be closed to form a horizontal 15° fan beam, with good resolution since its source is 1 mm×1 mm, in this example. The collimators may be rotated together through 52.5° to center the 15° fan beam onto a specified portion of the inspection target. The x-ray beam is now more concentrated by a factor of 6 compared to the 120° beam, but the effective source size is now close to 1 mm×3.5 mm and much of the concentration gain has been lost. The tube/collimator may be rotated so that the central axis of the beam points along the center of the 15° sweep. The inspection is now carried out with optimum resolution.

The rotation of the x-ray tube reduces the degradation of beam resolution at angles far from the axial direction. In some applications it may be advantageous to accept the degradation in resolution and increase the beam width to obtain as much flux as possible with that resolution. One method for doing so is to make the gap 185 of clamshell collimator 180 in an hour-glass shape, as shown in FIGS. 8A-8B, with the minimum opening of, for example, 3 mm in the center (for the central rays), increasing as a function of angle to either side of center. It should be borne in mind that maximizing the throughput does not equalize the flux throughput. When the finite size of the focal spot is taken into account, the intensity of the x-ray beam may vary by as much as a factor of 2 between its center and the extremes of +−55 degrees, such that the shaped collimator gap serves to equalize flux across the scan.

The embodiments of the invention described herein are intended to be merely exemplary; variations and modifications will be apparent to those skilled in the art. All such variations and modifications are intended to be within the scope of the present invention as defined in any appended claims. In particular, single device features may fulfill the requirements of separately recited elements of a claim.

What is claimed is:

1. A scanning apparatus for scanning a beam in a single dimensional scan, the apparatus comprising:
    a. a source of radiation for generating a fan beam of radiation effectively emanating from a source axis and characterized by a width;
    b. an angle selector, stationary during the course of scanning, for limiting the extent of the scan; and
    c. a multi-aperture unit rotatable about a central axis in such a manner that beam flux incident on a target is the same per revolution for different fields of view of the beam on the target,
wherein the multi-aperture unit includes an inner multi-aperture hoop characterized by a hoop axis, the inner multi-aperture hoop made of material opaque to the beam, and
wherein the inner multi-aperture hoop includes rings of apertures spaced laterally along the hoop axis in such a manner that axial motion of the multi-aperture hoop places a ring of apertures in the beam that is collimated by a corresponding opening angle in the angle selector.

2. A scanning apparatus in accordance with claim 1, further comprising a width collimator for collimating the width of the fan beam.

3. A scanning apparatus in accordance with claim 1, wherein the angle selector includes a slot of continuously variable opening.

4. A scanning apparatus in accordance with claim 1, wherein the central axis is substantially coincident with the source axis.

5. A scanning apparatus in accordance with claim 1, wherein the source axis is forward-offset relative to the central axis.

6. A scanning apparatus for scanning a beam in a single dimensional scan, the apparatus comprising:
    a. a source of radiation for generating a fan beam of radiation effectively emanating from a source axis and characterized by a width;
    b. an angle selector, stationary during the course of scanning, for limiting the extent of the scan:
    c. a multi-aperture unit rotatable about a central axis in such a manner that beam flux incident on a target is the same per revolution for different fields of view of the beam on the target; and,
    d. a width collimator for collimating the width of the fan beam,
wherein the width collimator includes a variable slot collimator, fixed during the course of scanning the beam, adapted to change the sweep angle of the beam, up to a specified maximum angle, and to change a central direction of the sweep.

7. A scanning apparatus in accordance with claim 1, wherein the source of radiation is an x-ray tube.

8. A scanning apparatus in accordance with claim 1, wherein the source of radiation is of a type generating a fan beam exceeding 60° in opening angle.

9. A scanning apparatus in accordance with claim 1, further comprising an enclosing conveyance for conveying the scanning apparatus past an inspection target.

10. A scanning apparatus in accordance with claim 1, wherein the scanning apparatus is coupled to a platform.

11. A scanning apparatus in accordance with claim 1, wherein the scanning apparatus is coupled to a platform in conjunction with at least one further scanning apparatus.

12. A scanning apparatus in accordance with claim 1, further comprising a filter disposed within the beam for changing the energy distribution of the beam.

13. A scanning apparatus in accordance with claim 1, wherein the multi-aperture unit includes two nested, multi-aperture collimators.

14. A scanning apparatus in accordance with claim 1, wherein the multi-aperture unit includes an inner multi-aperture hoop characterized by a hoop axis, the inner multi-aperture hoop made of material opaque to the beam.

15. A scanning apparatus in accordance with claim 1, wherein the inner multi-aperture hoop includes rings of apertures spaced laterally along a hoop axis in such a manner that axial motion of the multi-aperture hoop places a ring of apertures in the beam that is collimated by a corresponding opening angle in a slot collimator.

16. A scanning apparatus in accordance with claim 1, wherein the multi-aperture unit includes an outer multi-aperture hoop rotatable in registration with the inner multi-aperture hoop.

17. A scanning apparatus in accordance with claim 16, wherein the outer multi-aperture hoop includes a plurality of apertures configured as horizontal slots in such a manner as to define a minimum vertical size of emitted pencil beams.

18. A scanning apparatus in accordance with claim 16, wherein the inner multi-aperture hoop and the outer multi-aperture hoop are mechanically integral.

19. A scanning apparatus in accordance with claim 16, further comprising a variable width collimator for defining a width of the beam that enters the outer multi-aperture hoop.

20. A scanning apparatus in accordance with claim 1, wherein radiation is emitted through a plurality of apertures at different angles with respect to the target, such that pencil beams of penetrating radiation sweep in alternation through the target in such a manner as to provide a stereoscopic view of an interior volume of the target.

21. A scanning apparatus in accordance with claim 1, further comprising a rotation assembly adapted to provide for rotation of the source of radiation about the source axis.

22. A scanning apparatus in accordance with claim 1, wherein the multi-aperture unit includes substantially rectangular through-holes.

* * * * *